(12) United States Patent
Nakamura et al.

(10) Patent No.: US 8,354,064 B2
(45) Date of Patent: Jan. 15, 2013

(54) APPARATUS FOR PRODUCING LIPOSOMES AND METHOD OF PRODUCING LIPOSOMES

(75) Inventors: Koji Nakamura, Ashigarakami-gun (JP); Keisuke Yoshino, Ashigarakami-gun (JP); Yasuo Kurosaki, Ashigarakami-gun (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 124 days.

(21) Appl. No.: 12/935,430

(22) PCT Filed: Mar. 30, 2009

(86) PCT No.: PCT/JP2009/056483
§ 371 (c)(1),
(2), (4) Date: Sep. 29, 2010

(87) PCT Pub. No.: WO2009/123103
PCT Pub. Date: Oct. 8, 2009

(65) Prior Publication Data
US 2011/0024929 A1    Feb. 3, 2011

(30) Foreign Application Priority Data
Mar. 31, 2008  (JP) ................. 2008-091760

(51) Int. Cl.
*B01J 19/18* (2006.01)
(52) U.S. Cl. ......... 422/132; 422/130; 422/509; 436/164
(58) Field of Classification Search .................. 422/130, 422/131, 132, 501, 502, 504, 509, 513, 547; 436/164, 180
See application file for complete search history.

(56) References Cited

U.S. PATENT DOCUMENTS 4,551,288 A  * 11/1985  Kelly ............................ 264/4.6
5,795,506 A    8/1998  Hodosawa et al.
2002/0034748 A1 * 3/2002  Quake et al. ..................... 435/6
2003/0210985 A1 * 11/2003  Feygin et al. .................. 417/46

FOREIGN PATENT DOCUMENTS

JP          01-165935 A      6/1989
JP          8-266887 A      10/1996
JP        2007-007625 A      1/2007

OTHER PUBLICATIONS

Notification of Transmittal of Translation of the International Preliminary Report on Patentability (Form PCT/IB/338) dated Dec. 23, 2010, International Preliminary Report of Patentability (Form PCT/IB/373) and Written Opinion of the International Searching Authority (Form PCT/ISA/237) dated Dec. 13, 2010, issued in corresponding International Patent Application No. PCT/JP2009/056483.

* cited by examiner

*Primary Examiner* — Jill Warden
*Assistant Examiner* — Dwayne K Handy
(74) *Attorney, Agent, or Firm* — Buchanan Ingersoll & Rooney PC

(57) ABSTRACT

Disclosed herein are an apparatus for producing liposomes and a method of producing liposomes by which it is made possible to produce liposomes under sterile conditions during the manufacturing process while monitoring in line the particle diameter of liposomes. The apparatus for producing liposomes includes a unit for regulating the particle diameter of liposomes, a supply flow channel for supplying the particle diameter regulating unit with a solution under processing containing a liposome-forming lipid, and a discharge flow channel for discharging from the particle diameter regulating unit a solution under processing containing liposomes, the supply flow channel having an input port through which the solution under processing containing the liposome-forming lipid is put into the supply flow channel, wherein the discharge flow channel has a first light transmitting part at least a portion of which is made of material transparent to light, and also has at least a first light transmittance measuring unit which measures the light transmittance of the solution under processing containing liposomes by directing light to the first light-transmitting part from the outside of the first light-transmitting part. A method of producing liposomes by use of the apparatus.

7 Claims, 12 Drawing Sheets

◇ : 82.5mmol (PARTICLE DIAMETER=−0.9856×LASER TRANSMITTANCE+164.41, $R^2$=0.9845)
□ : 62.8mmol (PARTICLE DIAMETER=−1.1379×LASER TRANSMITTANCE+175.43, $R^2$=0.9951)
△ : 41.2mmol (PARTICLE DIAMETER=−1.2468×LASER TRANSMITTANCE+175.43, $R^2$=0.9801)
○ : 20.7mmol (PARTICLE DIAMETER=−1.5586×LASER TRANSMITTANCE+213.65, $R^2$=0.9392)

APPARATUS FOR PRODUCING LIPOSOMES AND METHOD OF PRODUCING LIPOSOMES

TECHNICAL FIELD

The present invention relates to a method of measuring the particle diameter of liposomes which is useful for drug delivery system, and to an apparatus for producing liposomes and a method of producing liposomes which employ the measuring method.

BACKGROUND ART

The drug delivery system (DDS) is one of the methods of enhancing the effect of pharmacotherapeutics. It employs a liposome preparation which is composed of vesicles of phospholipid bilayer structure and a drug supported thereby. The liposome preparation is now attracting keen attention because of its ability to support a drug on the liposome membrane or in the liposomal aqueous phase. It is common practice to chemically modify liposomes with functional groups, thereby changing liposomes into a prodrug which alters the drug's inherent behavior in blood such that the drug has an extended half-life and becomes stabilized in blood. Unfortunately, the prodrug prepared in this manner often exhibits toxicity and decreases in drug effect.

The foregoing disadvantage is overcome if a drug is supported by liposomes. In this case, liposomes help maintain the effect of the drug, extend the half-life of the drug, and improve the stability of the drug in blood, without noticeable side effects. The liposome preparation, with liposome's particle size adequately controlled and liposome's surface coated with a hydrophilic polymer, is not readily captured by the reticuloendotherial system (RES) present in the liver, spleen, lymph node, and lung, through which liposomes are excreted. Therefore, it stays longer in blood and accumulates in lesions (for passive targeting), thereby improving its therapeutic effect.

The pharmacokinetics of any drug enclosed in liposomes greatly is dependent on the behavior of liposomes in blood. In this case, it has been reported that the liposomal pharmacokinetics and distribution in the tissue are largely affected by the particle diameter and size distribution of liposomes. (See Non-Patent Document 1, for example.) These parameters are important for liposome preparations, and hence they are controlled in the particle size regulating step in the manufacturing process. Thus, the particle diameter regulation step is one of the most important steps in production of liposome preparations whose characteristic properties are determined by it.

The particle diameter of liposome preparations is established according to the object of therapy and the disease to be cured. To achieve the established particle diameter, the liposome forming step or the ensuing particle diameter regulating step was conducted. The particle diameter regulating step usually employs an extruder; it is repeated several times until the required particle diameter is achieved. The number of the particle diameter regulating steps is finally determined based on results of the liposomal diameter at each step obtained in the preliminary investigation for particle diameter regulating step. On the other hand, it has been reported that the particle diameter of liposomes varied depending on pressure applied in the particle diameter regulating step. (See Non-Patent Document 2, for example.) From above findings, if an excess pressure fluctuation occurs for some reason, the liposome with not-intended particle diameter is obtained. From this reason, there is no way of judging whether or not the desired particle diameter has been reached in the particle diameter regulating step in current known liposome production method.

Most liposome preparations are required to be germ-free because they are usually administered directly into the vein. Therefore, they should be produced under strictly sterile condition and germ related risk during manufacturing process should be reduced as far as possible. To meet this requirement, liposome preparations should be produced in a closed space because they cannot be sterilized after production. In practice, however, the production process for liposome is complicated and as specification as final product and intermediate product during manufacturing process, the particle diameter is set. Sampling of an intermediate product for measurement of particle diameter breaks the closed space and this procedure makes the sterile condition be endangered.

In order to provide liposome preparations of high quality, it is necessary to accomplish sterile operation and have a system for measuring and monitoring the particle diameter accurately in real time without contact with samples.

Meanwhile, the concept of Process Analytical Technology (PAT) is recently attracting attention. This concept has stemmed from the fact that the production technology tends to lag behind the technologies achieved in research and development and the underdeveloped production technology adversely affects product quality and quality control system, causing final products to be rejected. Thus it is necessary to apply the latest technology to the critical step that affects product quality in the manufacturing process so that the product is monitored continuously in real time to avoid rejections. Moreover, in this way it will be possible to simplify the off-line inspection step.

The measuring technique to which PAT is currently applied includes, for example, spectroscopic analysis by infrared absorption and Raman scattering, electronic sound spectroscopic analysis, X-ray spectroscopic analysis, pH measurement, conductivity measurement, potential measurement, and dielectric measurement. Among these techniques, spectroscopic analysis by near infrared absorption is widely used to determined mixing homogeneity, to measure moisture content, and to measure the content of specific components.

Non-Patent Document 1:
Biochim. Biophys. Acta. 1990, 99-107, 1994
Non-Patent Document 2:
Biophys. J. 74, 1996-3002, 1998

DISCLOSURE OF INVENTION

Technical Problem

One of the important steps in the production of liposome preparations is to control the particle diameter to ensure the product homogeneity.

In fact, however, the particle diameter of liposome is measured at a processing test only after the particle diameter regulating step but is not monitored in real time during processing.

The object of the present invention is to provide an apparatus and method for producing liposome under sterile conditions during the manufacturing process while monitoring in line the particle diameter of liposomes.

In addition, the apparatus according to the present invention is equipped with a system to estimate the particle size distribution of liposomes in a simple manner. This system helps produce liposome preparations of high quality.

Technical Solution

In order to address the problems mentioned above, the present inventors conducted a series of researches which lead to the finding that a system will be feasible to monitor the liposome formation in real time without contact in the particle diameter regulating stage when sample solutions containing liposomes are examined for transmittance by means of laser beam during the liposome production process. The present invention is based on this finding.

The present invention covers what is defined in paragraphs (1) to (8) below.

(1) An apparatus for producing liposomes, including:

a unit for regulating the particle diameter of liposomes, the unit having an inlet and an outlet;

a supply flow channel to supply the particle diameter regulating unit with a solution under processing containing a liposome-forming lipid, the supply flow channel being formed integrally with the particle diameter regulating unit through the inlet; and a discharge flow channel to discharge from the particle diameter regulating unit a solution under processing containing liposomes, the discharge flow channel being formed integrally with the particle diameter regulating unit through the outlet;

the supply flow channel having an input port through which the solution under processing containing the liposome-forming lipid is put into the supply flow channel;

wherein the discharge flow channel has a first light-transmitting part at least a portion of which is made of material transparent to light, and also has at least a first light transmittance measuring unit which measures the light transmittance of the solution under processing containing the liposomes by directing light to the first light-transmitting part from the outside of the first light-transmitting part.

The liposome producing apparatus as defined in paragraph (1) above is characterized in that the first light transmittance measuring unit is capable of displaying the light transmittance.

(2) The apparatus for producing liposomes as defined in paragraph (1) above, wherein a base end of the supply flow channel and a terminal end of the discharge flow channel are joined together so as to complete a circulating circuit for fluid.

(3) The apparatus for producing liposomes as defined in paragraph (1) or (2) above, wherein the supply flow channel has a second light-transmitting part at least a portion of which is made of material transparent to light, and also has a second light transmittance measuring unit which measures the light transmittance of the solution under processing containing the liposome-forming lipid by directing light to the second light-transmitting part from the outside of the second light-transmitting part.

The liposome producing apparatus as defined in paragraph (3) above is characterized in that the second light-transmittance measuring unit is capable of displaying the light transmittance of the solution under processing containing the liposome-forming lipid.

(4) The apparatus for producing liposomes as defined in paragraph (3) above, wherein the first light transmittance measuring unit has a first laser irradiating part, a first laser receiving part, and a first light transmittance calculating part connected to them, and the second light transmittance measuring unit has a second laser irradiating part, a second laser receiving part, and a second light transmittance calculating part connected to them.

(5) The apparatus for producing liposomes as defined in any of paragraphs (1) to (4) above, which further includes a unit for calculating the particle diameter of liposomes from the light transmittance.

(6) The apparatus for producing liposomes as defined in any of paragraphs (3) to (5) above, wherein the first light transmittance measuring unit displays the light transmittance of the solution under processing containing the liposomes and the second light transmittance measuring unit displays the light transmittance of the solution under processing containing said liposome-forming lipid.

(7) The apparatus for producing liposomes as defined in any of paragraphs (4) to (6) above, wherein the laser irradiating part emits a laser beam having a wavelength of 670 nm.

(8) A method of producing liposomes, including:

a preliminary step including passing a solution containing a liposome-forming lipid several times through a particle diameter regulating unit, thereby giving a liposome-containing solution, examining each liposome-containing solution, which has passed through the particle diameter regulating unit, for the light transmittance at a prescribed wavelength, examining each liposome-containing solution with an apparatus for measuring the particle diameter, which has passed through the particle diameter regulating unit, for the particle diameter of liposomes in the liposome-containing solution, and acquiring preliminarily the correlation between the light transmittance and the particle diameter; and a main step including causing the solution under processing containing a liposome-forming lipid to undergo particle diameter regulation by the apparatus for producing liposomes as defined in paragraphs (1) to (7) above, thereby giving a solution under processing containing liposomes, and producing liposomes while measuring the light transmittance of the solution under processing containing the liposomes at the prescribed wavelength.

The method of producing liposomes according to the present invention permits one to calculate the particle diameter of liposomes contained in the solution under processing containing the liposomes from the correlation obtained by the unit for calculating the diameter of liposomes and also from the light transmittance of the solution under processing containing the liposomes.

In addition, the present invention provides what is defined in paragraphs (9) and (10) below as a method of measuring the particle diameter of liposomes that can be used for the apparatus and method for production of liposomes according to the present invention.

(9) A method of measuring the particle diameter of liposomes by using an apparatus having a flow channel through which a liposome-containing solution under processing flows, at least a portion of the flow channel being a light transmitting part made of a transparent material, the apparatus being provided with a unit for measuring the light transmittance of the liposome-containing solution under processing that is passing through the flow channel, the light transmitting part being irradiated with light from outside thereof and also being provided with a unit for calculating the particle diameter of liposomes from the thus measured light transmittance.

(10) The method of measuring the particle diameter of liposomes as defined in paragraph (9) above, in which the unit for calculating the particle diameter of liposome calculates the particle diameter of liposomes contained in the liposome-containing solution under processing by using the correlation between the light transmittance and the particle diameter and the light transmittance of the liposome-containing solution under processing, the correlation being obtained by passing a solution containing a liposome-forming lipid several times through a particle diameter regulating unit, thereby changing it into a liposome-containing solution, examining each liposome-containing solution, which has passed through the particle diameter regulating unit, for the light transmittance at a prescribed wavelength, and examining each liposome-containing solution with an apparatus for measuring the particle diameter, which has passed through the particle diameter regulating unit, for the particle diameter of liposomes in the liposome-containing solution.

The apparatus and method for production of liposomes according to the present invention involve highly accurate measurement of the particle diameter of liposomes. This measuring technique is particularly applicable to the industry.

The result of the size differences obtained between before and after particle diameter regulating step at the particle size regulating stage can give the information for particle size distribution of liposomes.

In the course of completing the present invention, the present inventors were able to prepare liposomes in a completely closed line by continuously processing liposomes using a closed circulating system.

As a secondary effect, this system enables to monitor the particle diameter regulating step in real time, which leads to reduction of production time.

Advantageous Effects

The apparatus for producing liposomes according to the present invention permits one to produce liposomes in an in-line system under sterile conditions while monitoring the particle diameter of liposomes during the manufacturing process.

The method of producing liposomes according to the present invention permits one to produce liposomes in an in-line system under sterile conditions while monitoring the particle diameter of liposomes during the manufacturing process.

BEST MODE FOR CARRYING OUT THE INVENTION

Figure 1:
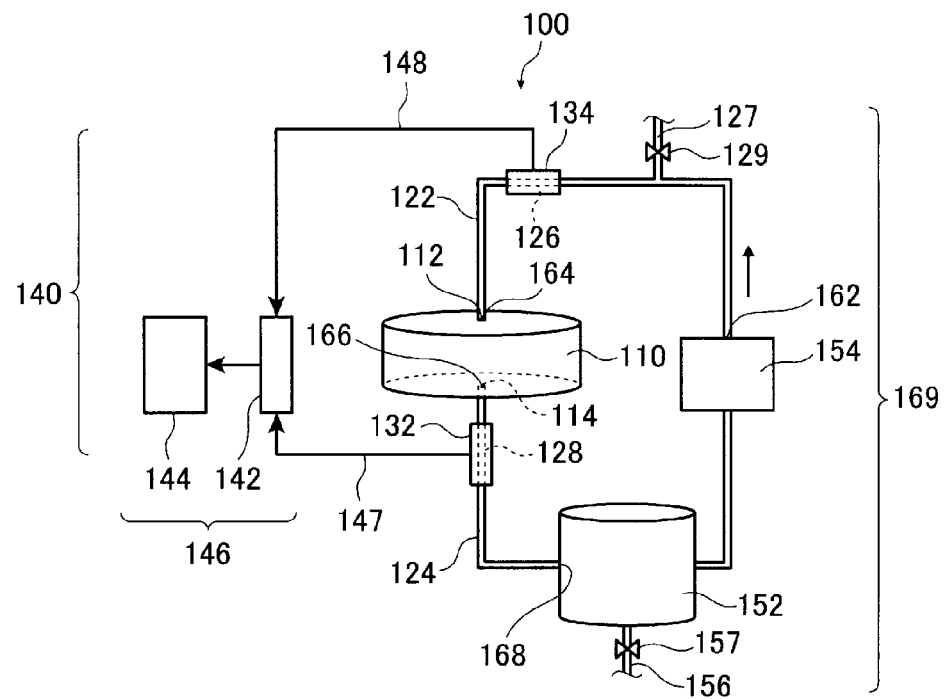
FIG. 1 is a schematic diagram illustrating one example of the apparatus for producing liposomes according to the present invention.

The following is a detailed description of the present invention.

What is mentioned first is about the method of measuring the particle diameter of liposome which is employed in the present invention as follows.

Two examples are listed below for the method of measuring the particle diameter of liposomes which can be employed in the present invention.

(1) The first method which relies on an apparatus for measuring the particle diameter of liposomes, the apparatus being composed of a flow channel which permits the liposome-containing solution under processing to pass through and which has a light transmitting part at least a portion of which is made of transparent material, and a unit for measuring the light transmittance of the solution under processing by directing light to the light transmitting part from the outside thereof.

(2) The second method which relies on an apparatus for measuring the particle diameter of liposomes, the apparatus having a unit for calculating the particle diameter of liposomes from the light transmittance mentioned above.

The following is a description of the unit for measuring the light transmittance.

The apparatus for measuring the particle diameter of liposomes is equipped with the unit for measuring the light transmittance. This unit is formed on the flow channel through which the liposome-containing solution under processing flows, and it also has a light-transmitting part at least a portion of which is made of a transparent material. This light transmitting part is irradiated with light from the outside thereof.

The light transmittance measuring unit is not specifically restricted so long as it is arranged on the outside of the light transmitting part (or the outside of the flow channel) and the light transmitting part is irradiated with light from the outside thereof, so that it is capable of measuring the light transmittance of the solution under processing. The light transmittance measuring unit is capable of displaying the light transmittance.

An example of the light transmittance measuring unit is one which is composed of a part that directs light to the light transmitting part from the outside thereof, a part that receives light that has passed through the light transmitting part, a part that is connected to the light irradiating part and the light receiving part and that calculates the light transmittance from the intensity of light directed from the light irradiating part and the intensity of light received by the light receiving part, and a part that displays the light transmittance.

The display part may be formed integrally with the light transmittance calculating part.

There are no specific restrictions on the way by which the display part displays the light transmittance.

Incidentally, the light transmittance measuring unit may be accommodated in a data collecting device which has the light transmittance calculating part as an external unit.

There are no specific restrictions on the light to be directed from the light irradiating part. The light includes, for example, laser beam, infrared rays, and X-rays.

The light may have any wavelength which is selected according to use, but the wavelength should preferably be determined according to the absorption spectrum of the object of measurement.

Since the present invention is basically designed for measurement of transmittance, the wavelength of the light should be selected, in general, within that of visible light (about 380 to 780 nm).

A laser beam is one preferred example of the light to be used for the light transmittance measuring unit.

The term "laser beam" used in the present invention implies a naturally nonexisting artificial light which is characterized by "monochromatism due to a single wavelength," "coherence due to equiphase," and "directivity due to the ability of light to converge without scattering."

The laser beam in common use for measurement of light transmittance is the one emanating from a red LED. It has a center wavelength of 630 to 680 nm; therefore, it is desirable that the laser beam used in the present invention should have a wavelength of 630 to 680 nm. However, this wavelength may be varied if it is necessary to adopt other wavelength according to the sample solution.

In the case where a laser beam is employed for measurement of light transmittance, the light transmittance measuring unit may be composed of a laser beam irradiating part, a laser beam receiving part, and a light transmittance calculating part connected to them.

The light transmittance measuring unit is arranged outside the light transmitting part which is attached to the flow channel through which the liposome-containing solution under processing passes and at least a portion of which is made of a transparent material.

The following is a description of the flow channel.

The flow channel is not specifically restricted so long as it permits the liposome-containing solution under processing to flow through the manufacturing line for liposome.

The flow channel may have a flow rate controlling unit (such as a caliber expanding unit and a temporary dwelling unit) and a sampling unit.

The liposome manufacturing line will be described later.

The liposome-containing solution under processing is not specifically restricted so long as it is a solution containing liposomes. The solution may be an aqueous solution or a solvent solution in an organic solvent or a mixture of water and an organic solvent.

The flow channel should have a light-transmitting part at least a portion of which is made of a transparent material.

In the case where the flow channel has a light transmitting part at least a portion of which is made of a transparent material, any other part than the light transmitting part should be made of an opaque material or a material which transmits light differently from that used for the light transmitting part.

In addition, the flow channel may be formed entirely from a transparent material.

The light transmitting part of the flow channel is made of a transparent material so that it allows measurement of light transmittance.

The transparent material is not specifically restricted so long as it has a high degree of transparency. It includes, for example, quartz glass, quartz crystal, glass, fluoroplastics (such as PFA), and plastics (such as polypropylene, polycarbonate, acrylic polymer, polystyrene, styrene-butadiene copolymer, styrene-acrylonitrile copolymer, acrylonitrile-butadiene-styrene copolymer, polyvinyl chloride, polysulfone, and polyester like PET).

The flow channel is not specifically restricted in shape; it may have a round, elliptic, or rectangular cross section.

In the case where the flow channel has at least partly the light transmitting part, the light transmitting part is not specifically restricted in shape so long as it does not hamper the light transmittance measuring unit from irradiating light or receiving light. For example, the flow channel may have the light irradiating part over the entire periphery thereof, or the flow channel may have two round, elliptical, or rectangular windows as the light irradiating part and the light receiving part.

In the case where the flow channel has at least partly the light transmitting part, the other parts than the light transmitting part are not specifically restricted in material; it may be formed from any material, like metal, which is opaque or nearly opaque to light.

In the case where the flow channel has at least partly the light transmitting part, the light transmitting part should preferably have a higher transparency than the other parts.

The light transmitting part should preferably be made of quartz glass or fluoroplastic. Quartz glass is known as a material which has a high transparency and finds use as optical fiber. Fluoroplastic, such as PFA (tetrafluoroethylene and perfluoroalkoxyethylene copolymer), has a high degree of transparency and a low degree of drug adsorption. The part other than the light transmitting part should preferably be made of stainless steel from the standpoint of manufacturing line, although its material is not specifically restricted.

The light transmittance measuring unit is not specifically restricted so long as it is arranged outside the light transmitting part. Also, in the case where the flow channel is entirely made of a transparent material, the light transmittance measuring unit is not specifically restricted in its position.

The space between the light transmittance measuring unit and the light transmitting part is not specifically restricted. They may be arranged such that they are in contact with each other or they are separate from each other.

In the case where there is a space between the light transmittance measuring unit and the flow channel, the space between the light irradiating part and the flow channel should be 0.1 to 100 cm and the space between the light receiving part and the flow channel should be 0.1 to 100 cm. The space should preferably be as short as possible for high accuracy from the practical point of view.

The following is a description (referred to the accompanying drawings) of the light transmittance measuring unit attached to the apparatus for measuring the particle diameter of liposomes which is used in the present invention and the flow channel provided with the apparatus for measuring the particle diameter of liposomes. The accompanying drawings are not intended to restrict the scope of the present invention.

Figure 3:
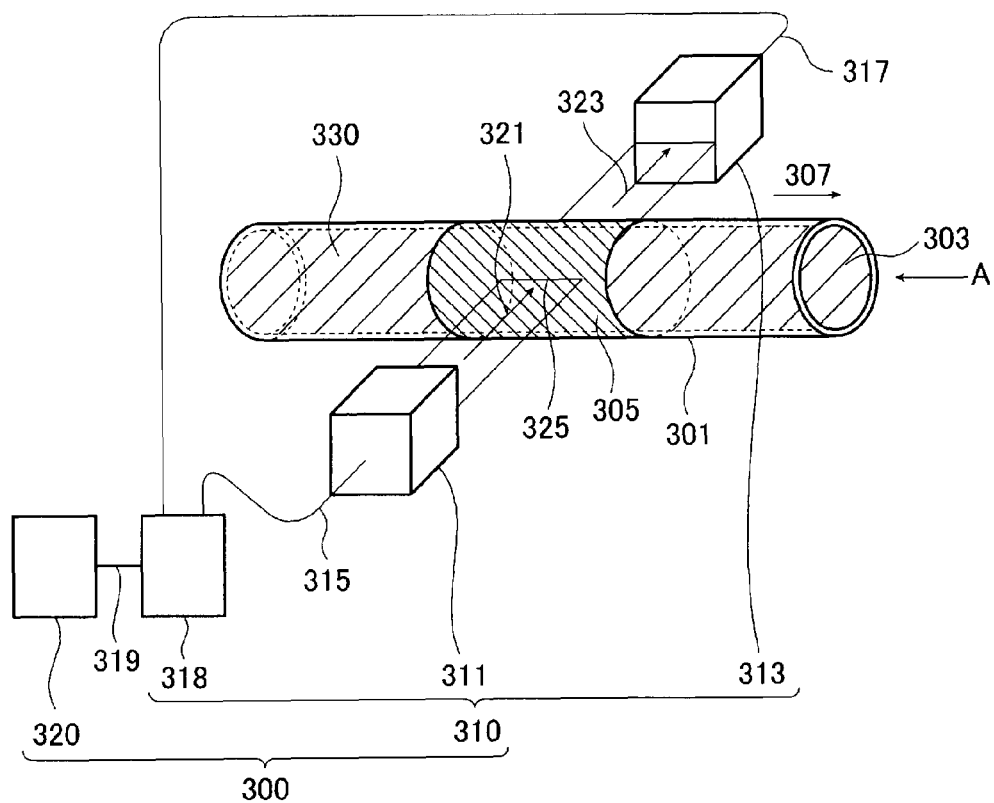
FIG. 3 is a schematic perspective view illustrating one example of a light transmittance measuring unit attached to the apparatus for measuring the particle diameter of liposomes which can be used in the present invention, and also illustrating the flow channel provided with the apparatus for measuring the particle diameter of liposomes.

FIG. 3 is a schematic perspective view illustrating one example of the light transmittance measuring unit attached to the apparatus for measuring the particle diameter of liposomes which is used in the present invention, and also illustrating the flow channel provided with the apparatus for measuring the particle diameter of liposomes.

In FIG. 3, a flow channel 301 permits a liposome-containing solution under processing 330 to flow through an inside 303 thereof in the direction of an arrow 307. The flow channel 301 has a light transmitting part 305 made of a transparent material. The flow channel 301 has a round cross section (not shown). The light transmitting part 305 constitutes the outer periphery of the flow channel which contains at least a part 325 to which a light 321 is directed.

The apparatus 300 for measuring the particle diameter of liposomes is composed of a light transmittance measuring unit 310 and a data collecting device 320.

The light transmittance measuring unit 310 is composed of a light irradiating part 311 (which directs the light 321 to the light transmitting part 305 from the outside thereof), the light receiving part 313 (which receives a light 323 that has passed through the light transmitting part 305), and a light transmittance calculating part 318 (which measures the light transmittance of the solution 330 under processing). The light transmittance calculating part 318 is connected to the light irradiating part 311 via a cord 315, to the light receiving part 313 via a cord 317, and to the data collecting device 320 via a cord 319.

The light transmittance is measured by the light transmittance measuring unit 310.

The thus measured light transmittance is displayed on the light transmittance calculating part 318 or the data collecting device 320.

Incidentally, in the case where the light transmittance measuring unit 310 is the first light transmittance measuring unit, the first light transmittance measuring unit 310 has the first light irradiating part 311, the first light receiving part 313, and the first light transmittance calculating part 318.

In the case where the light transmittance measuring unit 310 is the second light transmittance measuring unit, the second light transmittance measuring unit 310 has the second light irradiating part 311, the second light receiving part 313, and the second light transmittance calculating part 318.

The first light transmittance calculating part and the second light transmittance calculating part may be combined into one (not shown).

Figure 4:
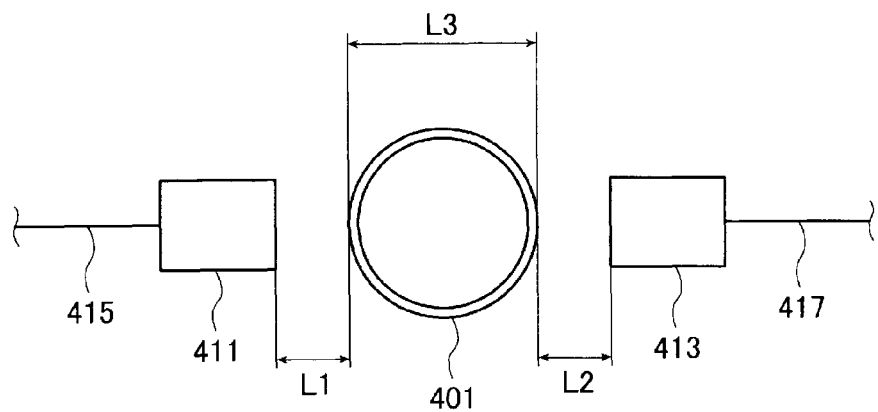
FIG. 4 is a side view (in the direction of arrow A in FIG. 3) illustrating one example of the light transmittance measuring unit attached to the apparatus for measuring the particle diameter of liposomes which can be used in the present invention, and also illustrating the flow channel provided with the apparatus for measuring the particle diameter of liposomes.

FIG. 4 is a side view (in the direction of arrow A in FIG. 3) schematically illustrating one example of the light transmittance measuring unit attached to the apparatus for measuring the particle diameter of liposomes which is used in the present invention, and also illustrating the flow channel provided with the apparatus for measuring the particle diameter of liposomes.

In FIG. 4, a flow channel 401 should preferably have a round cross section (not shown) whose outside diameter L3 is 0.5 to 100 cm. A light irradiating part 411 is connected to the light transmittance calculating part (not shown) via a cord 415, and a light receiving part 413 is connected to the light transmittance calculating part (not shown) via a cord 417. The space L1 between the light irradiating part 411 and the flow channel 401 should be 0.1 to 100 cm, and the space L2 between the light receiving part 413 and the flow channel 401 should be 0.1 to 100 cm.

Figure 5:
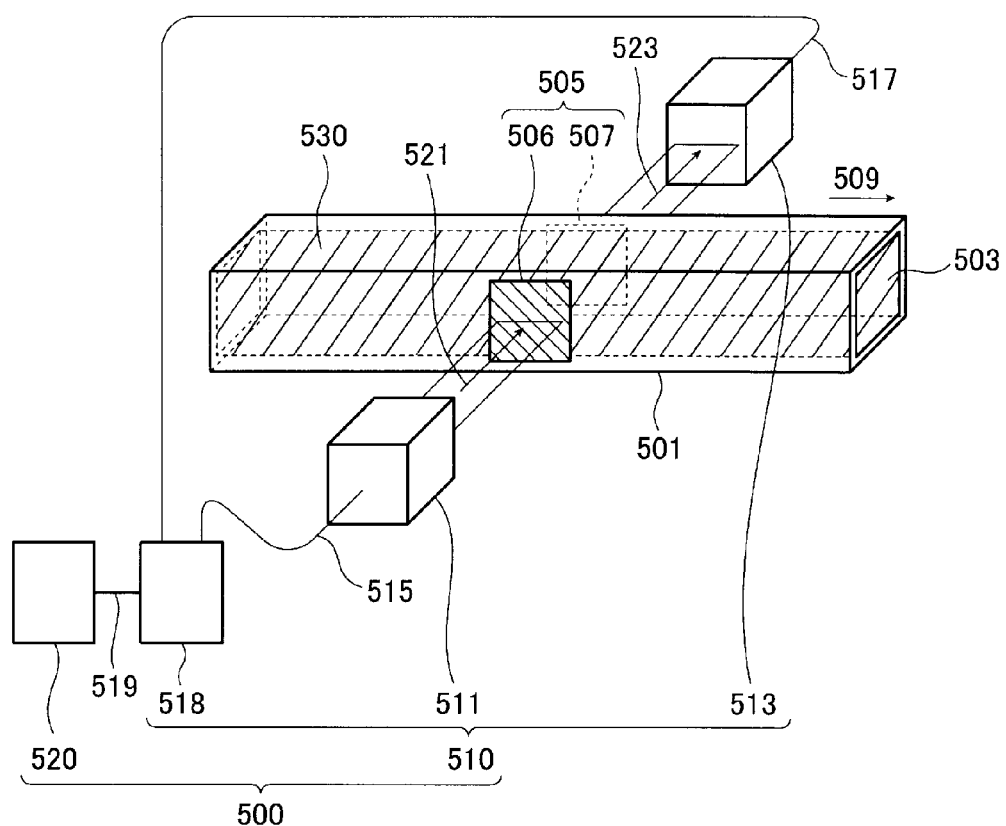
FIG. 5 is a schematic perspective view illustrating one example of the light transmittance measuring unit attached to the apparatus for measuring the particle diameter of liposomes which can be used in the present invention, and also illustrating the flow channel provided with the apparatus for measuring the particle diameter of liposomes.

FIG. 5 is a schematic perspective view illustrating one example of the light transmittance measuring unit attached to the apparatus for measuring the particle diameter of liposomes which is used in the present invention, and also illustrating the flow channel provided with the apparatus for measuring the particle diameter of liposomes.

In FIG. 5, a flow channel 501 permits a liposome-containing solution under processing 530 to flow through an inside 503 thereof in the direction of an arrow 509. The flow channel 501 has a light transmitting part 505 made of a transparent material. The light transmitting part 505 has a rectangular light exposure part 506 and a rectangular light transmitting part 507. The flow channel 501 has a rectangular cross section (not shown).

An apparatus 500 for measuring the particle diameter of liposomes is composed of a light transmittance measuring unit 510 and a data collecting device 520.

The light transmittance measuring unit 510 is composed of a light irradiating part 511 (which directs a light 521 to the light exposure part 506 from the outside thereof), a light receiving part 513 (which receives a light 523 that has passed through the light transmitting part 507), and a light transmittance calculating part 518 (which measures the light transmittance of the solution 530 under processing). The light transmittance calculating part 518 is connected to the light irradiating part 511 via a cord 515, to the light receiving part 513 via a cord 517, and to the data collecting device 520 via a cord 519.

The light transmittance is measured by the light transmittance measuring unit 510.

The thus measured light transmittance is displayed on the light transmittance calculating part 518 or the date collecting device 520.

The light transmittance measuring unit calculates (in the light transmittance calculating part) the light transmittance from the intensity of the light emitted from the light irradiating part and the intensity of the light received by the light receiving part. (The light transmittance is expressed in terms of percentage of the intensity of the light received by the light receiving part to the intensity of the light emitted from the light irradiating part.)

Incidentally, in the present invention, light transmittance may also be expressed as percent transmission.

The light transmittance calculating part is connected to the light irradiating part and the light receiving part. The connection of the light transmittance calculating part to the light irradiating part or the light receiving part may be by either wire circuit or wireless circuit, whose selection depends on the environment of installation and the conditions of operation.

Either a wire circuit or a wireless circuit may be used for the communication interface that is installed on the light transmittance measuring apparatus to be used for the light transmittance measuring unit and that is installed on the data collecting device which accommodates the unit for calculating the particle diameter of liposomes. Their selection depends on the environment of installation and the conditions of operation.

The following is a description of the unit for calculating the particle diameter of liposomes.

The method for measuring the particle diameter of liposomes according to the present invention employs the liposome particle diameter measuring apparatus which has the liposome particle diameter calculating unit to obtain the particle diameter of liposomes from the light transmittance mentioned above.

The method for measuring the particle diameter of liposomes according to the present invention is applied in such a way that the data of light transmittance collected by the light transmittance measuring unit is processed by the data collecting device (as an external unit) and converted into the value of particle diameter.

The unit for calculating the particle diameter of liposomes, preferably, calculates the particle diameter of liposomes contained in the liposome-containing solution under processing, by using the correlation between the light transmittance and the particle diameter, and the light transmittance of the liposome-containing solution under processing, the correlation being obtained by preliminarily passing a solution containing a liposome-forming lipid several times through a particle diameter regulating unit, thereby changing it into a liposome-containing solution, examining each liposome-containing solution, which has passed through the particle diameter regulating unit, for the light transmittance at a prescribed wavelength, and examining each liposome-containing solution with an apparatus for measuring the particle diameter, which has passed through the particle diameter regulating unit, for the particle diameter of liposomes in the liposome-containing solution.

The correlation is obtained from data of the light transmittance of the liposome-containing solution and data of the particle diameter of liposomes contained in the liposome-containing solution, the data being obtained in a preliminary step by passing a solution containing a liposome-forming lipid several times through a particle diameter regulating unit, thereby changing it into a liposome-containing solution, examining each liposome-containing solution, which has passed through the particle diameter regulating unit, for the light transmittance at a prescribed wavelength, and examining each liposome-containing solution with an apparatus for measuring the particle diameter, which has passed through the particle diameter regulating unit, for the particle diameter of liposomes in the liposome-containing solution.

The particle diameter regulating unit used in the preliminary step may be the one designed for batchwise operation or continuous operation.

The solution containing a liposome-forming lipid, which is used in the preliminary step, is not specifically restricted so long as it is a solution that contains such components as phospholipid capable of forming liposomes.

This solution should preferably be passed through the particle diameter regulating unit two to nine times.

In the present invention, the light transmittance of the liposome-containing solution was measured by using the transmittance device (Model No.: LX2-V10) made by Keyence Corp. The data collection was carried out by using the data collecting devices (Model No.: NR-HA08 and NR-500) made by Keyence Corp. The light transmittance was measured at a wavelength of 670 nm.

In the present invention, the particle diameter of liposomes contained in the liposome-containing solution was measured by using the apparatus for measuring the particle diameter "Zetasizer 3000" made by Malvern Instrument. The particle diameter of liposomes was measured by dynamic light scattering, and the resulting values were averaged to give the average particle diameter.

The particle size distribution of liposomes is expressed in terms of polydispersity index (which is obtained by dynamic light scattering with Zetasizer 3000 made by Malvern Instrument), and is also expressed in terms of the ratio (n/w) of the number-average particle diameter to the weight-average particle diameter which are measured with Field Flow Fractionation-Maltiangle Scattering (FFF-MALS, made by Whyatt Co., Ltd.).

The algorism for particle diameter conversion to give the correlation is not specifically restricted. A linear approximation is most desirable judging from the results obtained in the course of completion of the present invention.

The correlation between the light transmittance and the particle diameter may be obtained by the mathematical expression (I) below.

[Expression 1]

$$y_{(n)} = ax_{(n)} + b \qquad (I)$$

where, $y_{(n)}$ denotes the particle diameter of liposomes in the light transmitting part, a denotes a constant of proportionality, $x_{(n)}$ denotes the light transmittance in the light transmitting part calculated from the amount of light received which is measured at certain intervals, b denotes a constant, and n=0, 1, 2, . . . .

In the mathematical expression (I), the constants a and b vary depending on the concentration of the liposome-forming lipid contained in the solution containing a liposome-forming lipid.

For example, if the concentration of the liposome-forming lipid in the solution under processing is 82.5 mmol/L, the mathematical expression (I) becomes:

$$y_{(n)} = -1.0861 x_{(n)} + 173.89$$

Figure 10:
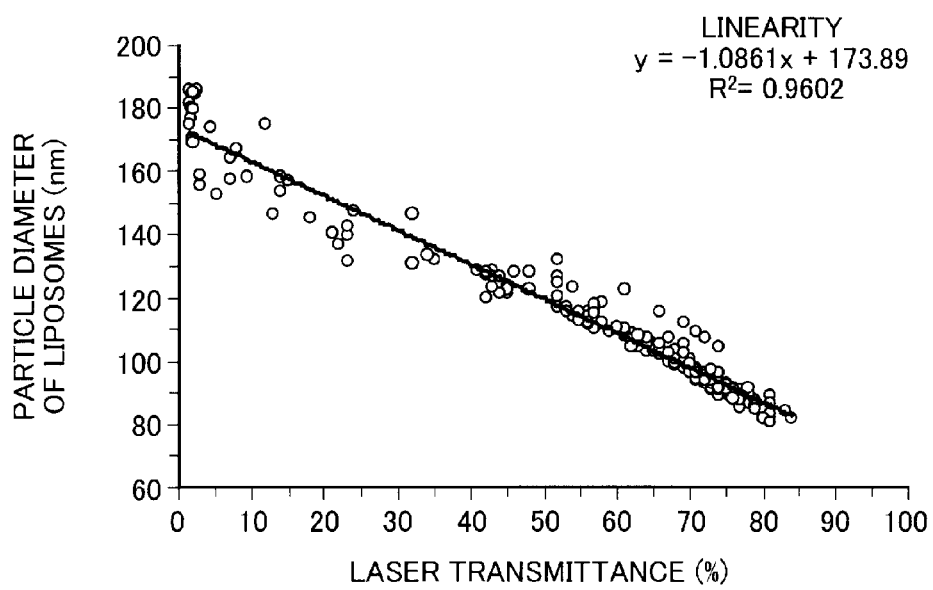
FIG. 10 is a graph showing the relationship between the particle diameter of liposomes at each step of particle diameter regulation and the laser transmittance in the preliminary step.

(see Example 1 and FIG. 10).

The mathematical expression (I) for the correlation is the one which is obtained in the preliminary step if the concentration of the liposome-forming lipid in the solution under processing containing the liposome-forming lipid that is used in the main step coincides with that in the preliminary step. The particle diameter of liposomes is predicted by substituting the light transmittance in the mathematical expression.

The following is a description of the method for measuring the particle diameter of liposomes that can be used in the present invention. The description is referred to the accompanying drawings, which are not intended to restrict the scope of the present invention.

Figure 2:
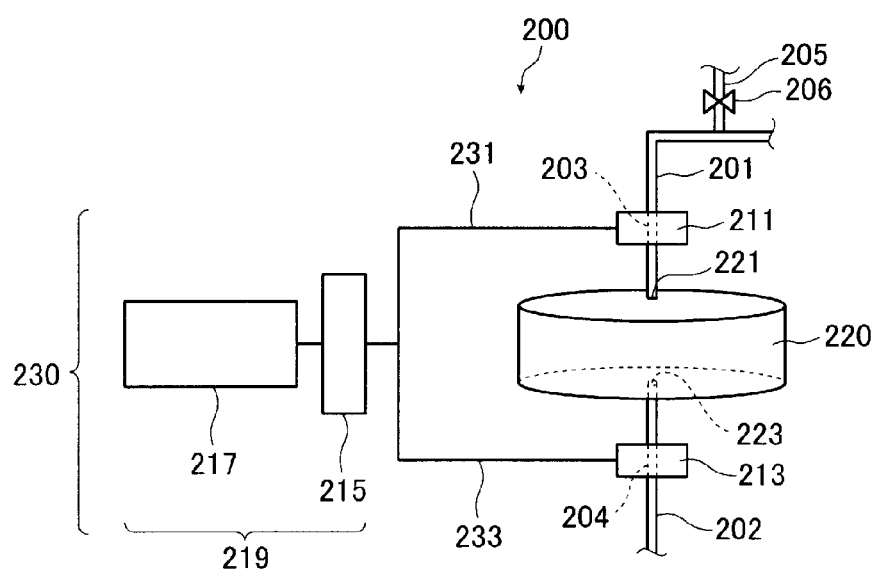
FIG. 2 is a schematic diagram illustrating one example of the method for measurement of the particle diameter of liposomes that can be employed in the present invention.

FIG. 2 is a schematic diagram illustrating one example of the method for measurement of the particle diameter of liposomes that can be employed in the present invention.

In FIG. 2, an apparatus 200 for production of liposomes has:

a particle diameter regulating unit 220 with an inlet 221 and an outlet 223;

a supply flow channel 201 which is integrally formed with the particle diameter regulating unit 220 through an inlet 221, and which supplies the particle diameter regulating unit 220 with a solution (not shown) under processing containing a liposome-forming lipid; and a discharge flow channel 202 which is integrally formed with the particle diameter regulating unit 220 through an outlet 223, and which discharges the solution under processing containing liposomes (not shown) from the particle diameter regulating unit 220;

wherein the supply flow channel 201 has an input port 205 through which the solution under processing containing a liposome-forming lipid (not shown) is input;

the discharge flow channel 202 has a first light transmitting part 204 at least a portion of which is made of a transparent material;

the supply flow channel 201 has a second light transmitting part 203 at least a portion of which is made of a transparent material; and the input port 205 has a valve 206, which opens and closes the input port 205.

The apparatus 200 for production of liposomes is equipped with an apparatus 230 for measurement of the particle diameter of liposomes.

The apparatus 230 for measurement of the particle diameter of liposomes has:

a first light transmittance measuring unit 213 which directs light toward the first light transmitting part 204 from the outside thereof so as to measure the light transmittance of the liposome-containing solution under processing (not shown);

a second light transmittance measuring unit 211 which directs light toward the second light transmitting part 203 from the outside thereof so as to measure the light transmittance of the liposome-containing solution under processing (not shown); and a data collecting device 219 equipped with a control unit 215 accommodating a unit for calculating the particle diameter of liposomes from the light transmittance and a data storage unit 217.

The light transmittance is measured by the first light transmittance measuring unit 213 and the second light transmittance measuring unit 211.

The thus measured light transmittance can be displayed on the first light transmittance measuring unit 213, the second light transmittance measuring unit 211 or the data collecting device 219.

The first light transmittance measuring unit 213 and the second light transmittance measuring unit 211 are connected to the data collecting device 219 through cords 231 and 233.

Each of the first light transmittance measuring unit 213 and the second light transmittance measuring unit 211 has a light irradiating part, a light receiving part, and a light transmittance calculating part (not shown). The light irradiating part (not shown) is actuated by signals from the control unit 215; it emits light, e.g., pulsed light at certain intervals.

While the liposome-containing solution under processing (not shown) is being discharged from the particle diameter regulating unit 220 to the discharge flow channel 202, the first light transmittance measuring unit 213 works in as follows: the light irradiating part (not shown) emits light, so that the light passes through the first light transmitting part 204, the light that has passed through the first light transmitting part 204 is received by the light receiving part (not shown), the signal in response to the intensity of received light is sent to the light transmittance ratio calculating part, the light transmittance calculating part calculates the light transmittance from time to time based on the ratio of the intensity of light received by the light receiving part to that of light emitted from the light irradiating part, the thus obtained light transmittance is sent to the data collecting device 219 and stored in the data storage unit 217.

After the start of production of liposomes in the particle diameter regulating unit 220, the control unit 215 performs calculations from time to time by substituting the light transmittance in the mathematical expression (1) below for prediction of the particle diameter, which is sent from the first light transmittance measuring unit 213, and the data of the obtained liposome diameter is stored in the data storage unit 217.

[Expression 2]

$$y_{1(n)} = a_1 x_{1(n)} + b_1 \quad (1)$$

where, $y_{1(n)}$ denotes the particle diameter of liposomes in the first light transmitting part, $a_1$ denotes a constant of proportionality, $x_{1(n)}$ denotes the light transmittance in the first light transmitting part calculated from the intensity of light received which is measured at certain intervals, $b_1$ denotes a constant, and n=0, 1, 2, . . . .

It can be confirmed if the obtained liposome reached the desirable diameter by plotting the relationship between the liposome particle diameter $y_{1(n)}$ and the time on a graph.

Besides, after the start of production of liposomes in the particle diameter regulating unit 220, the control unit 215 performs calculations from time to time by substituting the light transmittance in the mathematical expression (2) below for predication of the particle diameter of liposomes, which is sent from the second light transmittance measuring unit 211, and the thus data of obtained particle diameter of liposomes is stored in the data storage unit 217.

[Expression 3]

$$y_{2(n)} = a_1 x_{2(n)} + b_1 \quad (2)$$

where, $y_{2(n)}$ denotes the particle diameter of liposomes in the second light transmitting part, $a_1$ denotes a constant of proportionality, $x_{2(n)}$ denotes the light transmittance in the second light transmitting part calculated from the intensity of light received which is measured at certain intervals, $b_1$ denotes a constant, and n=0, 1, 2, . . . .

The control unit 215 performs calculations from time to time to predict the particle size distribution of liposomes according to the mathematical expression (3) below and the results are stored in the data storage unit 217.

[Expression 4]

$$\text{Differences of light transmittance} = x_{1(n)} - x_{2(n)} \quad (3)$$

When the relationship between the difference in light transmittance and the actually measured data of particle size distribution measured at each time separately is plotted on a graph, it is possible to predict the particle size distribution of liposomes thus obtained.

The following is a description of the manufacturing line for liposomes.

The manufacturing line for liposomes usually includes a homogenizing step, a liposome forming step, a step of removing the unenclosed drug, and a sterile step in this order.

In the present invention, the flow channel is not specifically restricted so long as it constitutes a portion of the manufacturing line through which the liposome-containing solution under processing passes.

Therefore, in the present invention, the liposome-containing solution under processing denotes the one which is obtained in the steps that follow the liposome-forming step. Incidentally, in the case where the liposome-forming step optionally includes a particle diameter regulating step and a step of modification with a hydrophilic polymer that follow a step of forming crude liposomes, the solution that is obtained after the step of forming crude liposomes is also designated as the liposome-containing solution under processing.

In liposome production, if the light transmittance measuring unit is placed anywhere around the flow channel to pass the liposome-containing solution under processing after the liposome-forming step, it is not specifically restricted.

However, it should preferably be placed after the particle diameter regulating step from the standpoint of observing the change in liposome particles. It should most preferably be placed in front and behind the particle diameter regulating apparatus to be used for the particle diameter regulating step.

The number of the light transmittance measuring unit to be placed is one or more, preferably two or more.

The light transmittance measuring unit is placed at the position shown in the accompanying drawings, which are not intended to restrict the scope of the present invention.

Figure 6:
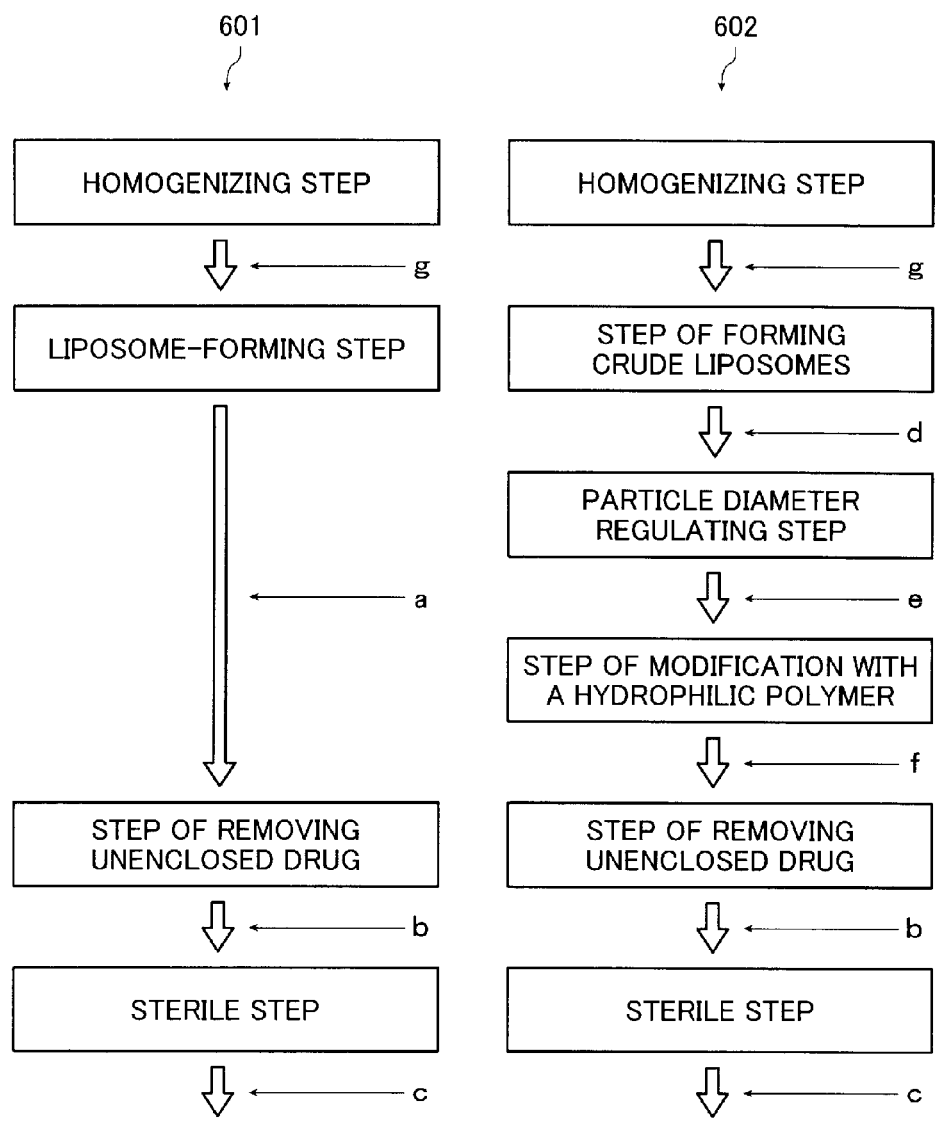
FIG. 6 is a flow chart illustrating the manufacturing line for liposomes.

FIG. 6 is a flow chart illustrating the manufacturing line for liposomes as one example.

In FIG. 6, a liposome manufacturing line 601 has the homogenizing step, the liposome-forming step, the step of removing the unenclosed drug, and the sterile step. The apparatuses (not shown) used in the individual steps are sequentially connected by the flow channels g, and a-c. Of them, liposome-containing solution under processing passes through the flow channels a, b, and c, which connect the apparatuses (not shown) used in the individual steps that follow the liposome-forming step.

In the present invention, the solution obtained by the homogenizing step in the preliminary step corresponds to the solution containing a liposome-forming lipid.

Also, the solution obtained by the homogenizing step in the main step corresponds to the solution under processing containing a liposome-forming lipid.

In the present invention, the solution obtained by the liposome-forming step in the main step corresponds to the liposome-containing solution.

Also, the solution obtained by the liposome-forming step in the main step corresponds to the solution under processing containing liposomes.

Besides, in FIG. 6, the liposome manufacturing line 602 has a homogenizing step, a liposome forming step, a step of removing the unenclosed drug, and the sterile step, and the liposome-forming step includes a particle diameter regulating step and a step of modification with a hydrophilic polymer which follow the step of forming crude liposomes.

In the case where the liposome-forming step includes the particle diameter regulating step and the step of modification with a hydrophilic polymer which follow the step of forming crude liposomes, the liposome-containing solution under processing passes through the flow channels d-f, b, and c.

Incidentally, in the present invention, the drug is enclosed in liposomes by any one of the following ways. The drug to be enclosed is added to the solution under processing containing a liposome-forming lipid in the liposome-forming step, so that the drug is enclosed simultaneously with liposome formation. The drug is added to the outside of the liposome membrane and then allowed to migrate into the solution within the liposome membrane along the gradient of ion concentration (across the liposome membrane) which has been previously made after the step of liposome formation, so that the drug is enclosed in liposomes. The sequence of these steps is not specifically restricted in the present invention.

Incidentally, although there are the cases wherein the step of replacing the external solution including the step of removing the unenclosed drug is repeated twice and a freeze-dry step is employed in the methods of ion concentration gradient and others, these duplicated and additional steps do not affect the scope of the present invention.

The following is a description of the steps included in the method of producing liposomes.

The homogenizing step denotes a step of dissolving a liposome-forming lipid capable of forming liposome membrane in an organic solvent, and allowing individual components to disperse uniformly.

The liposome-forming lipid is usually composed of a plurality of lipids such as phospholipid and cholesterol. In the case where there exist plurality of liposome-forming lipids, it is desirable to employ a homogenizing step in order to prevent the liposome-forming lipid from becoming inhomogeneous in liposome formation. In the case where a single liposome-forming lipid is used, the homogenizing step is not necessarily essential, but it is desirable to employ the homogenizing step explained below. A well-known homogenizing method is the thin-membrane method which is composed of completely dissolving the lipid in chloroform or the like and vacuum-drying the resulting solution. In large-scaled liposome production methods, the following method is widely employed; the liposome-forming lipid is completely dissolved into organic solvent like alcohol including ethanol etc to be homogenized, and the resultant, the liposome-forming lipid-organic solvent, is used in next step, liposome forming step, and finally the organic solvent is removed from the resultant by utilizing the heat yielded during the liposome forming step or substitution step of an external solution.

The liposome-forming step is composed of two substeps: a first one for forming crude liposomes with not-controlled particle diameters from a homogenized lipid (crude liposome-forming step), and a subsequently conducted second one for regulating the particle diameters of crude liposomes (particle diameter regulating step). The particle diameter regulating step may optionally be followed by a step of modifying liposomes with a hydrophilic polymer.

In the present invention, the liposome-forming step in the production of liposomes is referred to as a "main step."

Several methods have been reported about the method for producing crude liposomes. They include hydration method (Bangham method), ultrasonic treating method, and reverse phase evaporation method. Other methods intended for industrial production include heating method and lipid dissolving method. DRV (Dehydrated/Rehydrated Vesicles) method and freeze-thaw method have been reported as one way of increasing the amount of the drug to be retained in the internal aqueous phase.

In the liposome-forming step, the particle diameter of liposomes is regulated by any known technique such as membrane emulsification and high-pressure emulsification (which keeps application of high shear force) in the particle diameter regulating step. The former is accomplished by passing the solution through filters several times, and the latter is accomplished by allowing the solution to be discharged under high pressure. These methods are described in "Liposome Technology, Liposome Preparation, and Related Techniques" 2nd edition, vol. I-III, CRC Press, compiled by G. Gregoriadis. Citation from this book will serve as a description herein.

Recently developed technologies include jet emulsification and liposome production by use of supercritical carbon dioxide. The former employs the change in velocity due to compression under super-high pressure that generates a jet flow for emulsification by shearing. In addition, a modified ethanol pouring method has recently been developed to simplify the particle diameter regulating step.

In the present invention, these methods can be used as the particle diameter regulating unit in the liposome-forming step.

One example of the apparatus for producing liposomes, which is used in the particle diameter regulating step, has:

a unit of regulating the particle diameter of liposomes, the unit having an inlet and an outlet;

a supply flow channel to supply the particle diameter regulating unit with a solution under processing containing a liposome-forming lipid, the supply flow channel being formed integrally with the particle diameter regulating unit through the inlet; and a discharge flow channel to discharge from the particle diameter regulating unit a solution under processing containing liposomes, the discharge flow channel being formed integrally with the particle diameter regulating unit through the outlet;

wherein the supply flow channel has an input port through which the solution under processing containing the liposome-forming lipid is put into the supply flow channel, and the discharge flow channel has a first light-transmitting part at least a portion of which is made of material transparent to light.

The particle diameter regulating unit most commonly employs an extruder to regulate the particle diameter of liposomes. The following is a detailed description of the method that employs an extruder as a unit for regulating the particle diameter of liposomes.

It is possible to obtain liposomes having a properly regulated particle diameter by using an extruder in the following manner. The first step is to prepare a solution containing a lipid (dispersed therein) capable of forming liposome membrane. In the next step, this solution is made by stirring into a solution containing crude liposomes. Finally, the thus prepared solution is passed through a filter having pores corresponding to the desired particle diameter of liposomes. The foregoing process is simpler than any other manufacturing processes, and it is widely applicable, ranging from laboratory scale to industrial scale.

There are no specific restrictions on the extruder to be used to regulate the particle diameter of liposomes in the particle diameter regulating step. Any known extruder may be used so long as it has a filter inside.

The filter inside the extruder is not specifically restricted on the filter mesh, arrangement, or material.

Regulation of particle diameter by an extruder may be accomplished by any of various methods.

Examples of the methods include continuous operation, batchwise operation, and parallel operation with a plurality of extruders.

The following is a description of the method for particle diameter regulation by batchwise operation.

Particle diameter regulation by batchwise operation is accomplished by transferring the stock solution from one tank to another through filters in multiple stages.

It is not specifically restricted for the filter mesh, arrangement or materials of filters equipped inside of extruder in the diameter regulation by batchwise operation.

The apparatus for producing liposomes that employs the particle diameter regulation by batchwise operation is described below with reference to the accompanying drawings, which are not intended to restrict the scope of the present invention.

Figure 7:
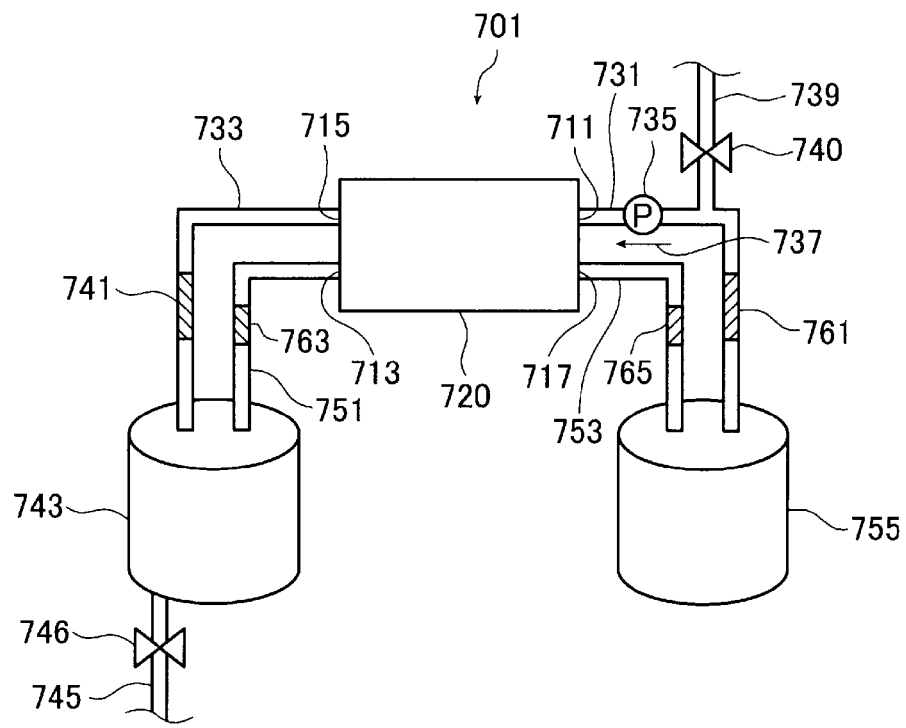
FIG. 7 is a schematic diagram illustrating one example of the apparatus for producing liposomes which is used for particle diameter regulation in batchwise operation.

FIG. 7 is a schematic diagram illustrating one example of the apparatus for producing liposomes which is used for particle diameter regulation in batchwise operation.

In FIG. 7, an apparatus 701 for production of liposomes which is used for particle diameter regulation in batchwise operation has:

a unit 720 for regulating the particle diameter of liposomes with inlets 711 and 713, and outlets 715 and 717;

a supply flow channel 731 which is integrally formed with the particle diameter regulating unit 720 through the inlet 711, and which supplies the particle diameter regulating unit 720 with a solution (not shown) under processing containing a liposome-forming lipid; and a discharge flow channel 733 which is integrally formed with the particle diameter regulating unit 720 through the outlet 715, and which discharges from the particle diameter regulating unit 720 the solution (not shown) under processing containing liposomes;

wherein the supply flow channel 731 has an input port 739 for the solution (not shown) under processing containing a liposome-forming lipid to be input therein.

The discharge flow channel 733 has a first light transmitting part 741 at least a portion of which is made of a transparent material; and the discharge flow channel 733 is connected to a tank 743, which stores the solution (not shown) under processing containing liposomes.

To the tank 743 is connected a supply flow channel 751 which supplies the particle diameter regulating unit 720 with the solution (not shown) under processing containing liposomes. The supply flow channel 751 is formed integrally with the particle diameter regulating unit 720 through the inlet 713. The particle regulating unit 720 is integrally formed with a discharge channel 753 through the outlet 717. The discharge channel 753 is connected to a tank 755, in which the solution (not shown) under processing containing liposomes is stored.

The tank 743 has a discharge outlet 745 to discharge the solution (not shown) under processing containing liposomes from the apparatus for producing liposomes. The discharge outlet 745 can be opened and closed by a valve 746.

The input port 739 has a valve 740, and the input port 739 can be opened and closed by the valve 740.

The supply flow channel 731 has a pump 735, and the pump 735 feeds the solution under processing containing a liposome-forming lipid in the direction of an arrow 737 and can circulate the solution under processing containing liposomes in the direction of arrow 737.

The apparatus 701 for production of liposomes may have second to fourth light transmitting parts 761, 763, and 765.

The following is a description of the method for continuous particle diameter regulation which serves as a unit for regulating the particle diameter of liposomes.

According to the method for continuous particle diameter regulation, the liposome-containing solution (liposome dispersion) under processing is supplied from one tank, passed through an extruder, returned to the same tank, and finally supplied to the extruder again, thereby regulating the particle diameter.

The apparatus for producing liposomes which is used for continuous particle diameter regulation will be described below with reference to the accompanying drawings, which are not intended to restrict the scope of the present invention.

Figure 8:
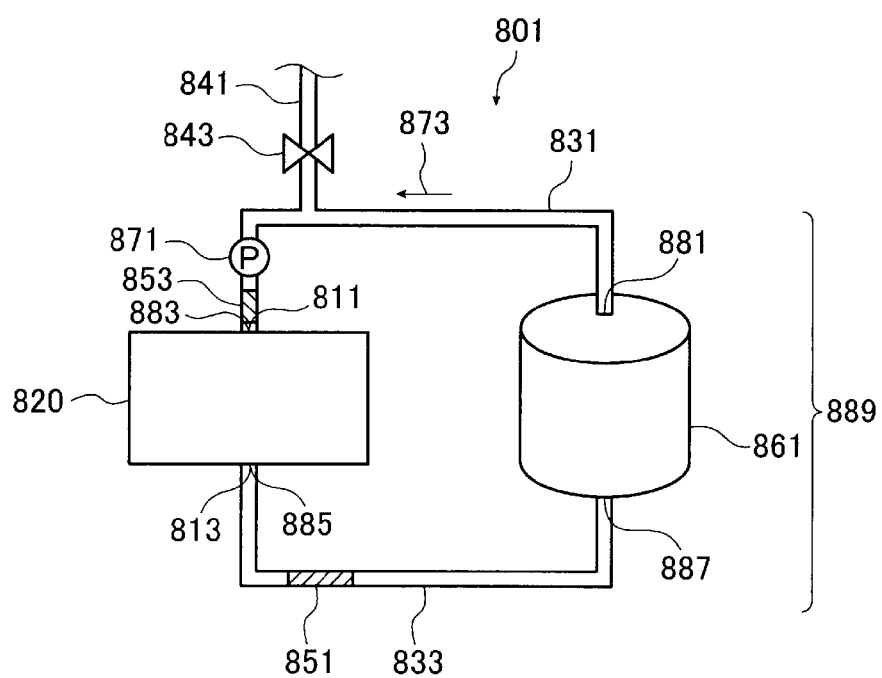
FIG. 8 is a schematic diagram illustrating one example of the apparatus for producing liposomes which is used for particle diameter regulation in continuous operation.

FIG. 8 is a schematic diagram illustrating one example of the apparatus for producing liposomes which is used for particle diameter regulation in continuous operation.

In FIG. 8, an apparatus 801 for production of liposomes which is used for particle diameter regulation in continuous operation has:

a unit 820 for regulating the particle diameter of liposomes with an inlet 811 and an outlet 813;

a supply flow channel 831 which is formed at a terminal end 883 integrally with the particle diameter regulating unit 820 through the inlet 811, and which supplies the particle diameter regulating unit 820 with the solution (not shown) under processing containing a liposome-forming lipid; and a discharge flow channel 833 which is formed at a base end 885 integrally with the particle diameter regulating unit 820 through the outlet 813, and which discharges from the particle diameter regulating unit 820 the solution (not shown) under processing containing liposomes;

wherein the supply flow channel 831 has an input port 841 for the solution (not shown) under processing containing a liposome-forming lipid to be input in the supply channel 831, and the discharge flow channel 833 has a first light transmitting part 851 at least a portion of which is made of a transparent material, and a base end 881 of the supply flow channel 831 and a terminal end 887 of the discharge flow channel 833 are connected to each other through a tank 861, so that they form a fluid circulating circuit 889.

The input port 841 has a valve 843, and the input port 841 can be opened and closed by the valve 843.

The fluid circulating circuit 889 has a pump 871, and the pump 871 feeds the solution under processing containing a liposome-forming lipid in the direction of an arrow 873 and also circulates the solution under processing containing liposomes in the direction of arrow 873.

The apparatus 801 for production of liposomes may have a second light transmitting part 853.

The apparatus for producing liposomes which is used for particle diameter regulation in continuous operation may constitute the closed circulating system.

The closed circulating system mentioned later is suitable for the particle diameter regulation by an extruder from the standpoint of particle size distribution.

Incidentally, the closed circulating system used in the present invention denotes one which is constructed such that the solution (liposome dispersion) under processing containing liposomes is supplied from one tank and passed through an extruder and finally returned to the same tank.

The particle diameter regulating step can be followed by a step of modification with a hydrophilic polymer.

The step of modification with a hydrophilic polymer can modify the outer surface of the liposome with a hydrophilic polymer. Modification of the liposome's outer surface with a hydrophilic polymer is accomplished by bringing liposomes into contact with a hydrophilic polymer and then immobilizing the hydrophilic polymer onto the liposome's outer surface. Immobilization may be facilitated by providing the liposome's outer surface with sites for immobilization of a hydrophilic polymer or by providing the hydrophilic polymer with sites for immobilization on the liposome's outer surface. In the present invention, the term "hydrophilic polymer" embraces any polymer which has sites for immobilization on the liposome's outer surface, in addition to the hydrophilic polymer itself.

In the step of modification with a hydrophilic polymer, it is desirable to use the hydrophilic polymer in the form of solution. The solvent in which the hydrophilic polymer is dissolved is not specifically restricted. Considering the necessity to mix with water, solvents such as water, alcohols, DMF, THF, and DMSO are desirable, among which water is most desirable.

In the step of modification with a hydrophilic polymer, the hydrophilic polymer should preferably be added at a temperature not lower than the phase transition temperature of the main material constituting the liposome membrane. The phase transition temperature of the main material constituting the liposome membrane depends on the structure of the lipid. It is usual to use a phospholipid having a phase transition temperature not lower than the temperature (35 to 37° C.) in the living body. To be concrete, the main material constituting the liposome membrane should preferably have a phase transition temperature not lower than 50° C. In this case, the hydrophilic polymer should be added at a temperature not lower than 50° C.

After addition in the step of modification with a hydrophilic polymer, the resulting solution should be heated and stirred at a temperature higher than the phase transition temperature. Duration of stirring should be 0 to 120 minutes, preferably 0 to 60 minutes, and more preferably 0 to 45 minutes.

After the step of modification with a hydrophilic polymer, preferably, the liposome after the step of modification with hydrophilic polymer should preferably be cooled rapidly from the standpoint of the stability of lipid. A more convenient way of cooling is by ice-cooling. The unbound hydrophilic polymer in the step of modification with a hydrophilic polymer can be removed in the subsequent step of removing the unenclosed drug. Therefore, the step of modification with a hydrophilic polymer should preferably be followed by the step of removing the unenclosed drug.

The step of removing the unenclosed drug is intended to remove the unenclosed drug after the step of forming liposomes with a drug solution. The step of replacing the external solution of liposomes is intended to replace the external solution in the case where the liposome forming step using the solution without drug are conducted. The object of replacing the external solution is to remove the organic solvent which has been brought during the liposome forming step that follows the homogenizing step. Another object is to create the ion gradient across the liposome membrane. The step of removing the unenclosed drug and the step of replacing the external solution are useful also as the step of removing the hydrophilic polymer which has remained unbound. In the main step, it is possible to remove that part of the hydrophilic polymer which remains unbound out of the hydrophilic polymer added in the step of modification with a hydrophilic polymer. The step of removal may be accomplished by a known method such as dialysis, ultracentrifugation, or gel filtration. For commercial intended production methods, the foregoing techniques are practiced by using hollow fibers such as dialyzer, or tangential flow or diafiltration through ultrafiltration membranes.

The sterile step is intended to perform sterilization after the step of forming liposomes. The method for sterilization is not specifically restricted. It includes sterilization by filtration, sterilization by high-pressure steam, sterilization by dry heating, sterilization by radiation (such as electron rays, X-rays, and γ-rays), sterilization by ozone water, and sterilization by hydrogen peroxide. The sterilization may be omitted depending on the manufacturing method. Sterilization by filtration is a desirable mode of the sterile step.

The method of filtration sterilization requires that the filter allows liposomes to pass through but does not allow *Brevundimonas diminuta* (about 0.3×0.8 μm in size) used as index organisms. Therefore, the size of liposomes should be sufficiently smaller than that of *Brevundimonas diminuta*. It is important for conducting the sterile filtration step without fail that the liposomal size is around 100 nm. The filter for filtration sterilization should have a pore diameter not larger than 0.45 μm, say 0.2 μm.

The step of forming liposomes should preferably be incorporated with the step of regulating the particle diameter of liposomes. In the case where liposomes take on a spherical or nearly spherical shape, the diameter of liposomes should be normally 20 to 2000 nm, preferably 30 to 400 nm, more preferably 50 to 250 nm, although it is not specifically restricted.

The following is a description of the ingredients to be used for production of liposomes.

A liposome is a closed vesicle which has a phospholipid bilayer and has an aqueous phase (internal aqueous phase) in the inside space of vesicle.

The term "liposome" used herein may also imply liposome pharmaceutical preparations that drug is entrapped into liposomes.

In addition, the term "liposome" used herein may denote not only liposome particles itself but also a suspension of liposome particles.

The term "supported" used herein means that a drug is contained in the carrier. To be concrete, it expresses a state of a drug existing in the internal aqueous phase of liposomes, a state of a drug being electrostatically immobilized on the surface layer of lipid as a constituent of the carrier, or a state of a drug being partly or entirely contained in the layer of lipid. The place where a drug is supported is the surface of liposomes, the membrane of lipid, or the internal aqueous phase. The internal aqueous phase is most desirable because it has a large volume and hence is capable of supporting a large amount of drugs. The liposome pharmaceutical preparations are not specifically restricted so long as they are in such a state that the drug is supported by liposomes. They may also exist as the dispersed or suspended state in the solution under processing.

It is known that liposomes have the membrane structure including unilamellar vesicle (Small Unilamellar Vesicle, SUV, Large Unilamellar Vesicle (LUV)) composed of single membrane of lipid bilayer and multilamellar vesicle (MLV) composed of more than one membrane of lipid bilayer. The MLV is the suitable layer structure which effectively prevents the entrapped drug into liposomes from leaking.

The liposome-forming lipid is not specifically restricted so long as it is capable of forming liposomes. It includes, for example, phospholipids, other lipids than phospholipids, derivatives thereof, and lipid derivatives of hydrophilic polymers.

The phospholipid used for production of liposomes is commonly an amphipathic substance having the hydrophobic group composed of long-chain alkyl groups within molecule, and hydrophilic groups composed of phosphoric acid groups.

Examples of the phospholipid include glycerophospholipid (such as phosphatidylcholine (=lecithin), phosphatidylglycerol, phosphatidylic acid, phosphatidylethanolamine, phosphatidylserine, and phosphatidylinositol), sphingo phospholipid (such as sphingomyelin, SM), natural or synthetic diphosphatidyl phospholipid (such as cardiolipin) and derivatives thereof, and hydrogenated products thereof (such as hydrogenated soybean phosphatidylcholine, HSPC). These phospholipids will be referred to also as "phospholipids" hereinafter. Of these examples, hydrogenated phosholipids (such as hydrogenated soybean phosphatidylcholine) and sphingomyelin are preferable.

The phospholipid to be used for liposomes should be one which forms the main membrane of liposomes whose phase transition temperature is higher than the temperature (35 to 37° C.) of the living body, so that the drug entrapped in liposomes does not easily escape from liposomes in blood or during storage. Such liposomes should be prepared at a temperature higher than the phase transition temperature of the main membrane because it is difficult to regulate the particle diameter at a temperature lower than the phase transition point of the main membrane. In the case where the phase transition temperature of the material for the main membrane is about 50° C., it is preferable to produce liposomes at about 50 to 80° C., specifically about 60 to 70° C.

The liposomes may contain, as the material for the main membrane, one kind or more than one kind of phospholipid.

The amount of the phospholipid as the major constituent should be normally 20 to 100 mol %, preferably 40 to 100 mol %, based on the total amount of the lipid constituting the membrane.

Also, the amount of other lipids than phospholipids should be normally 0 to 80 mol %, preferably 0 to 60 mol %, based on the total amount of the lipid constituting the membrane.

In the present invention, the hydrophilic polymer can modify the bilayer, and bilayer surfaces, particularly its outer surface alone selectively.

The hydrophilic polymer to be used for modification is not specifically restricted. It includes, for example, polyethylene glycol, Ficoll, polyvinyl alcohol, styrene-maleic anhydride alternating copolymer, divinyl ether-maleic anhydride alternating copolymer, polyvinylpyrrolidone, polyvinyl methyl ether, polyvinylmethyloxazoline, polyethyloxazoline, polyhydroxypropyloxazoline, polyhydroxypropylmethacrylamide, polymethacrylamide, polydimethylacrylamide, polyhydroxypropyl methacrylate, polyhydroxyethyl acrylate, hydroxymethyl cellulose, hydroxyethyl cellulose, polyaspartamide, and synthetic polyamino acids.

Of these examples, polyethylene glycols, polyglycerins, and polypropylene glycols are preferable because they make the pharmaceutical preparations of liposomes stay long in blood and hence they meet the object of the present invention. Particularly preferable among them are polyethylene glycol (PEG), polyglycerin (PG), and polypropylene glycol (PPG). The hydrophilic polymer mentioned above may have its one terminal alkoxylated (e.g., methoxylated, ethoxylated, or propoxylated) for their improvement in storage stability. Most desirable among the foregoing hydrophilic polymers is polyethylene glycol (PEG) because of its widespread availability and its ability to improve retentivity in blood.

The liposomes may contain other components than phospholipid and lipid derivatives of hydrophilic polymer which constitute their membrane. Such additional components include lipids and their derivatives other than such phospholipids as cholesterol and saturated/unsaturated fatty acids (which will be occasionally referred to as "other lipids" hereinafter). The membrane of the liposomes should preferably be formed from the foregoing phospholipid and lipid derivative of hydrophilic polymer as the main component and a mixture of lipids containing other lipids. The liposomes pertaining to the present invention may contain, in addition to the foregoing lipids and hydrophilic polymer, other membrane components capable of forming the foregoing membrane structure, in an amount not harmful to the object of the present invention.

The liposomes can support various kinds of therapeutic drugs as exemplified below.

Nucleic acids, polynucleotides, genes and analogs thereof, anticancer drugs, antibiotics, enzyme preparations, antioxidants, lipid uptake inhibitors, hormone preparations, antiflammatory drugs, steroid preparations, vasodilators, andiotensin-converting enzyme inhibitors, angiotensin receptor antagonists, inhibitors for proliferation and migration of smooth muscle cells, antiplatelet drugs, anticoagulants, chemical mediator release inhibitors, drugs for promoting or suppressing proliferation of vascular endothelial cells, aldose reductase inhibitors, inhibitors for proliferation of mesangial cells, lipoxygenase inhibitors, immunosuppressants, immunostimulants, antiviral drugs, Maillard reaction inhibitors, amyloidosis inhibitors, nitrogen monoxide synthesis inhibitors, AGEs (advanced glycation endproducts) inhibitors, radical scavengers, proteins, peptides, glycosaminoglycan and derivatives thereof, oligosaccharides, and polysaccharides.

Typical examples are listed below. Anticancer drugs, such as anthracycline group (including doxorubicin, daunorubicin, and epirubicin), cisplatin group (including cisplatin and oxaliplatin), taxene group (including paclitaxel and docetaxel), vincalkaloid group (including vincristine and vinblastine), bleomycin group (including bleomycin), and cirolimus group (including cirolimus). Antimetabolites, such as methotrexate, fluorouracil, gemcitabine, and cytarabine. Peptide drugs, such as hemoglobin, interferon, and insulin. Adrenocorticosteroids and derivatives thereof, such as spicamycine derivatives, porphyrin compounds, predonisolone, methylpredonisolone, and dexamethasone. Nonsteroidal antiinflammatory drugs, such as aspirin, indometacin, ibuprofen, mefanamic acid, and phenylbutazone. Inhibitors for proliferation of mesangial cells, such as heparin and low-molecular weight heparin. Immunosuppressants, such as ciclosporin. ACE (agiotensin converting enzyme) inhibitors, such as captopril. AGE (advanced glycation endproduct) inhibitors, such as methyl guanidine. TGF-β antagonists, such as biglycan and decoline. PKC (protein kinase C) inhibitors. Prostaglandin preparations, such as $PGE_1$ and $PGI_2$. Peripheral vasodilator, such as papaverine, nicotinic acid, tocopherol, and calcium antagonist. Phosphodiesterase inhibitors. Antithrombotic drugs, such as ticlopidine and aspirin. Anticoagulants, such as warfarin, heparin, and antithrombic drug. Thrombolytics such as urokinase. Radical scavengers, such as chemical mediator release inhibitors, antibiotics, antioxidants, enzyme preparations, lipid uptake inhibitors, hormone preparations, vitamin C, Vitamin E, and SOD. Antisense oligonucleotide (to inhibit proliferation of mesanginal cells), decoy, and gene.

The liposomes may also contain diagnostic reagents such as X-ray contrast medium, ultrasonic diagnostic reagent, diagnostic reagent for nuclear medicine with radioisotope labeling, and diagnostic reagent for nuclear magnetic resonance.

The liposomes may further contain, in addition to the foregoing drugs, stabilizers, antioxidants, osmoregulating chemicals, and pH adjusters, which are medicinally permissible depending on the route of administration.

The apparatus for producing liposomes according to the present invention will be described below with reference to the accompanying drawings, which are not intended to restrict the scope of the present invention.

FIG. 1 is a schematic diagram illustrating one example of the apparatus for producing liposomes according to the present invention.

In FIG. 1, an apparatus 100 for production of liposomes has: a unit 110 for regulating the particle diameter of liposomes with an inlet 112 and an outlet 114;

a supply flow channel 122, which is integrally formed with the particle diameter regulating unit 110 through the inlet 112 at a terminal end 164 and which supplies the particle diameter regulating unit 110 with the solution (not shown) under processing which contains a liposome-forming lipid; and a discharge flow channel 124, which is formed integrally with the particle diameter regulating unit 110 through the outlet 114 at a base end 166 and which discharges the solution under processing which contains liposomes from the particle diameter regulating unit 110;

wherein the supply flow channel 122 has an input port 127 through which the solution (not shown) under processing which contains a liposome-forming lipid is input, the input port 127 is opened and closed by a valve 129, the supply flow channel 122 has a second light transmitting part 126 at least a portion of which is made of a transparent material;

the discharge flow channel 124 has a first light transmitting part 128 at least a portion of which is made of a transparent material;

a base end 162 of the supply flow channel 122 is connected to a terminal end 168 of the discharge flow channel 124 through a tank 152 and a pump 154, so that a fluid circulating channel 169 is constructed; and the tank 152 has a discharge port 156 through which the solution under processing (which contains liposomes) is discharged from the apparatus 100 for production of liposomes, the discharge port 156 being opened and closed by a valve 157.

The apparatus 100 for production of liposomes is provided with an apparatus 140 for measurement of the particle diameter of liposomes, and the apparatus 140 for measurement of the particle diameter of liposomes has: a first light transmittance measuring unit 132, which directs light toward a first light transmitting part 128 from the outside thereof so as to measure the light transmittance of the liposome-containing solution under processing (not shown);

a second light transmittance measuring unit 134, which directs light toward a second light transmitting part 126 from the outside thereof so as to measure the light transmittance of the liposome-containing solution under processing (not shown); and a data collecting device 146 accommodating a unit for calculating the particle diameter of liposomes from the light transmittance, the data collecting device 146 having a control unit 142 and a data storage unit 144.

The first light transmittance measuring unit 132 and the second light transmittance measuring unit 134 are connected to each other through a data collecting device 146, and cords 147 and 148.

The first light transmittance measuring unit 132 has a first light irradiating part, a first light receiving part, and a first light transmittance calculating part (not shown).

The second light transmittance measuring unit 134 has a second light irradiating part, a second light receiving part, and a second light transmittance calculating part (not shown).

The light irradiating part (not shown) is actuated by signals from the control unit 142; it emits light (for example, pulsed light) at certain intervals.

While the liposome-containing solution under processing (not shown) is being discharged from the particle diameter regulating unit 110 to the discharge flow channel 124, the first light transmittance measuring unit 132 works in the following way. The light irradiating part (not shown) emits light, so that the light passes through the first light transmitting part 128. The light that has passed through the first light transmitting part 128 is received by the light receiving part (not shown), the signal in response to the intensity of received light send to the light transmittance calculating part (not shown). The light transmittance calculating part calculates the light transmittance from time to time based on the ratio of the intensity of light received by the light receiving part to that of light emitted from the light irradiating part. The thus obtained light transmittance is sent to the data collecting device 146 and stored in the data storage unit 144.

The light transmittance can be displayed on the first light transmittance measuring unit 132, the second light transmittance measuring unit 134, or the data collecting device 146.

After the start of production of liposomes in the particle diameter regulating unit 110, the control unit 142 performs calculations from time to time by substituting the light transmittance in the mathematical expression (1) for prediction of the particle diameter of liposomes, which is sent from the first light transmittance unit 132. The thus obtained particle diameter of liposomes is stored in the data storage unit 144.

The data collecting device 146 can display the thus obtained data of the particle diameter of liposomes.

Besides, after the start of production of liposomes in the particle diameter regulating unit 110, the control unit 142 performs calculations from time to time by substituting the light transmittance in the mathematical expression (2) for prediction of the particle diameter of liposomes, which is sent from the second transmittance measuring unit 134. The thus obtained particle diameter of liposomes is stored in the data storage unit 144.

The data collecting device 146 can display the thus obtained data of the particle diameter of liposomes.

The control unit 142 calculates from time to time to predict the particle size distribution of liposomes according to the mathematical expression (3) based on the light transmittances at the first light transmitting part 128 and the second light transmitting part 126. The results are stored in the data storage unit 144.

The data collecting device 146 can display the thus obtained data.

The apparatus for producing liposomes according to the present invention should preferably have the light transmittance measuring unit (which has the laser irradiating part, the laser receiving part, and the light transmittance calculating part) built thereinto. Moreover, it should preferably be installed in a sterile room.

Besides, in the present invention, the data collecting device can not only work for data collection and monitoring but also function as a single control system combined with the particle diameter regulating apparatus. For example, in the case where apparently the data collecting apparatus find it to be clearly close to the intended particle, this information is sent to the particle diameter regulation apparatus and the this apparatus can control the rate of solution feeding or stop the feeding automatically.

The term "particle diameter monitoring system" used herein denotes a system which is able to monitor the particle diameter of liposomes contained in the liposome-containing solution under processing, the monitoring being accomplished by measuring in line the light transmittance of the liposome-containing solution under processing which is produced by the apparatus and method for production of liposomes according to the present invention.

The particle diameter is measured usually by laser diffraction/scattering or dynamic/static light scattering. The apparatus in general use for measurement of particle diameter utilizes laser.

However, the principle of measurement is very complicated, and the particle diameter thus measured varies depending on the method of analysis. Therefore, it is necessary to measure the particle diameter according to the established method of analysis. Measurement may occasionally take several minutes.

Therefore, it is substantially difficult to measure particle diameter in real time by using the foregoing apparatus for measurement of particle diameter.

By contrast, the method for measurement of particle diameter according to the present invention differs from the conventional one mentioned above. It obtains the particle diameter from the mathematical expression following the relationship between the data of particle diameter obtained from the previously selected particle diameter measuring apparatus and the continuously measured transmittance of the laser beam. It does not need any complicated formula, and the relationship with the good linearity and the highly accuracy of prediction are given.

According to the present invention, the method for measurement of the particle diameter of liposomes permits measurement to be performed at any intervals, of the order of microseconds at a minimum.

For this reason, the method of producing liposomes according to the present invention is capable of monitoring in real time the particle diameter of liposomes while the particle diameter of liposomes is being regulated.

The apparatus for producing liposomes according to the present invention can observe the particle diameter of liposomes in the liposome-containing solution under processing by monitoring the light transmittance of it, and is capable of in-line manufacturing the liposome keeping the sterile condition.

According to the method of producing liposomes in the present invention, observation of the diameter of drug-enclosed liposomes in the liposome-containing solution under processing can be conducted by monitoring the transmittance of the solution under processing containing liposome, the liposomes can be manufactured under the sterile condition in line.

EXAMPLES

The invention will be described in more detail with reference to the following examples and test examples, which are not intended to restrict the scope thereof.

The liposome preparations prepared in each example or sampled in the course of particle diameter regulation were examined for average particle diameter by dynamic light scattering method with Zetasizer 3000, made by Malvern Instruments Inc.

The particle size distribution is expressed in terms of polydispersity index (which is obtained by dynamic light scattering) as well as in terms of the ratio of number- and weight-average particle diameter which is obtained by Field Flow Fractionation-Maltiangle Scattering (FFF-MALS of Whyatt Corp.).

In the examples, particle diameter regulation was accomplished with the help of Emulsiflex C50 (made by Avestin Co., Ltd.).

In the examples, the supply flow channel and discharge flow channel are metal tubes having a round cross section, 2 cm in inside diameter and 3 cm in outside diameter. They have a light transmitting part in a portion thereof which is a transparent polypropylene tube, 100 cm long.

In the examples, both the light irradiating part and the light receiving part of the light transmittance measuring device are placed 1 cm away from the supply flow channel or the discharge flow channel.

The light transmittance measuring apparatus and the data collecting device, which were used in the examples, are specified below.

Light transmittance measuring apparatus (for measurement with laser beam): Model LX2-V10, made by Keyence Corp.

Data collecting device: Model NR-HA08, NR-500, made by Keyence Corp.

Wavelength of laser beam used in the examples: 670 nm

Listed below are the abbreviation and molecular weight of each component used in the examples.

Hydrogenated soybean lecithin (HSPC, M.W. 790)
Cholesterol (M.W. 386.66)
Polyethylene glycol$_{5000}$-distearoylphosphatidyl-diethanolamine (PEG$_{5000}$-DSPE, M.W. 6031)

<Scatter of Particle Diameter of Liposomes, in Production of Liposomes with Particle Diameter Regulation by Continuous Operation>

(1) Homogenizing Step

A mixture of hydrogenated soybean lecithin (HSPC) (35.0 g) and cholesterol (15.0 g) was given absolute ethanol (50 mL), followed by dissolution with heating. This procedure was repeated twice to prepare lot-1 and lot-2.

(2) Step of Preparation of Crude Liposomes

The ethanol solution of lipids obtained in the homogenizing step was given 450 mL of aqueous solution of ammonium sulfate (250 mM) heated at 65 to 75° C. The resulting mixture was stirred to give a dispersion of crude liposomes.

(3) Step of Regulation of Particle Diameter

In the particle diameter regulating line Emulsiflex C50 (made by Avestin Corp.) was employed as the particle diameter regulating methods. The manufacturing line for continuous operation as shown in FIG. 8 was assembled and the liposomes obtained in the crude liposome-forming step was supplied in it. FIG. 8 is a schematic diagram illustrating one example of the apparatus for producing liposomes which is used for particle diameter regulation in continuous operation. This apparatus is provided with three sets of polycarbonate filters (made by Whatman Co., Ltd.), each set consisting of two stacked filters with a pore size of 0.4, 0.3, and 0.1 μm placed on the upper stream side and downstream side in the direction of flow. The two lots underwent particle size regulation individually. After the start of particle size regulation, samples (10 mL each) were taken as a function of time (2.5, 5, 7.5, 10, 15, 20, and 30 minutes). Incidentally, the particle diameter regulating unit was supplied with the dispersion of crude liposomes at a pressure of 10 MPa. The results are shown in FIG. 9.

(4) Step of Modification with a Hydrophilic Polymer

An aqueous solution containing 7.69 g of PEG$_{5000}$-DSPE in 200 mL of water was prepared. (This solution serves as washing water for reverse osmosis membrane.) After heating to 65° C., 2 mL of the PEG$_{5000}$-DSPE solution was added to the liposomes prepared in the particle diameter regulating step mentioned above. The resulting dispersion of liposomes was heated to introduce PEG$_{5000}$-DSPE into liposomes. (The amount of PEG$_{5000}$-DSPE introduced was 0.75 mol %.) After the heating was over, the dispersion of liposomes was rapidly cooled with ice.

Figure 9:
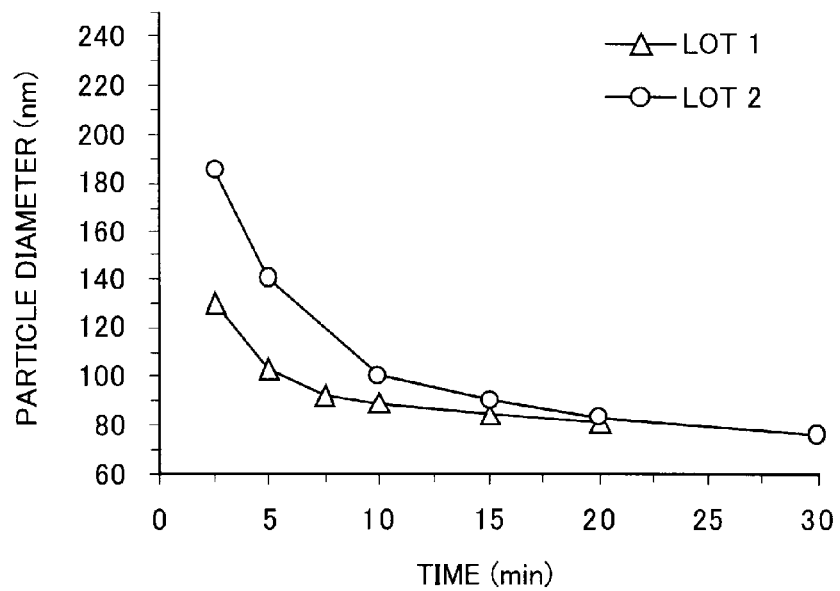
FIG. 9 is a graph showing the relationship between the duration of particle diameter regulation and the particle diameter of liposomes produced by continuous particle diameter regulation.

FIG. 9 is showing the particle diameter reduction curve obtained in the step of particle diameter regulation by continuous operation following the prescription mentioned above.

FIG. 9 is a graph showing the relationship between the duration of particle diameter regulation and the particle diameter of liposomes produced by continuous particle diameter regulation.

It is apparent from FIG. 9 that, in the graph showing the particle diameter reduction curve, the liposomes differ in particle diameter even though they were prepared under the same conditions.

Incidentally, though not shown in this example, the particle diameter of liposomes formed in the case of using batchwise particle diameter regulation method as the particle diameter regulating unit was also investigated, like that obtained by the continuous particle diameter regulation. In this case, also, it was confirmed that the liposomes obtained differ in particle diameter even though they were produced with the same formulation and under the same operating conditions.

Example 1

Relationship Between Transmittance and Particle Diameter which is Used for Particle Diameter Monitoring System According to the Present Invention The following apparatuses were used in this and other examples.

Apparatus for measurement of light transmittance: Model LX2-V10, made by Keyence Corp., operated with laser beam.

Data collecting device: Model NR-HA08 and NR-500, made by Keyence Corp.

Wavelength of laser beam: 670 nm.

(1) Mounting of Particle Diameter Monitoring System

After assembling the particle diameter regulation line for batchwise operation as shown in FIG. 7, the particle diameter monitoring system was equipped with it as shown in FIG. 2.

FIG. 2 is a schematic diagram illustrating one example of the method for measurement of the particle diameter of liposomes that can be employed in the present invention.

FIG. 7 is a schematic diagram illustrating one example of the apparatus for producing liposomes which is used for particle diameter regulation in batchwise operation.

That is, the extruder was installed in the filter holder (not shown), and the light transmittance measuring apparatuses were attached to the inlet and the outlet of the filter holder of the particle diameter regulating line as shown in FIG. 2 so that they could direct and receive laser beam to and from the liposome suspension flowing through the particle diameter regulating line.

(2) Correction of the Particle Diameter Monitoring System

The particle diameter regulating line was washed with about 5 liters of water. During this washing process, the light transmittance of laser was measured and the thus measured value was regarded as 100% for correction of the particle diameter monitoring system.

(3) Homogenizing Step

HSPC and cholesterol were weighed so that their molar ratio was 54:46, with the total amount of lipids being 82.5 mmol. Absolute ethanol was added to the lipids such that the ratio of the former to the latter is 1 mL to 1 g, approximately. The lipids were dissolved in ethanol by heating.

(4) Step of Preparing Crude Liposomes

A solution of ammonium sulfate (250 mM) was prepared. To the solution prepared in the homogenizing step was added the ammonium sulfate solution (heated to 65 to 75° C.) so that the resulting solution contained 10% ethanol.

(5) Step of Particle Diameter Regulation

The crude liposomes obtained in the step of preparing crude liposomes was incorporated into the particle diameter regulating line. In this step, polycarbonate filters, each having a pore diameter of 0.4, 0.2, and 0.1 μm, were in combination used to regulate the particle diameter. The particle diameter regulating step was repeated nine times (at a maximum). Sampling (10 mL) was performed in each stage of particle diameter regulation. During particle diameter regulation, the data collecting device displayed the values of laser transmittance. These values were recorded. Incidentally, during the particle diameter regulating step, the sample solution was fed at a pressure of 10 MPa. The results are shown in FIG. 10.

(6) Step of Modification with a Hydrophilic Polymer

The previously prepared aqueous solution containing 7.69 g of $PEG_{5000}$-DSPE in 200 mL of RO water, which had been heated to 65° C., was added to the sample (2 mL) of liposomes obtained in the particle diameter regulating step. The resulting dispersion was heated at 60 to 70° C. so that $PEG_{5000}$-DSPE was introduced into liposomes. (The amount introduced was 0.75 mol %.) After the heating was over, the liposome dispersion was cooled rapidly with ice.

FIG. 10 is a graph showing the relationship between the particle diameter of liposomes at each step of the particle diameter regulation and the laser transmittance.

It is apparent from FIG. 10 that there is a linear relationship between the particle diameter of liposomes and the laser transmittance with the correlation coefficient ($r^2$) being as high as 0.9602.

In other words, there is a high correlation between the particle diameter of liposomes and the laser transmittance.

It was also found that it is possible to accurately predict the particle diameter of liposomes by using the formula of correlation shown in FIG. 10.

Example 2

Influence of Lipid Concentration on Correlation Between Particle Diameter and Laser Transmittance (1) Mounting of Particle Diameter Monitoring System After the particle diameter regulating line for continuous operation was assembled as shown in FIG. 8, it was equipped with the particle diameter monitoring system as shown in FIG. 2. That is, the extruder was set in the filter holder (not shown), and the light transmittance measuring apparatuses were attached to the inlet and the outlet of the filter holder of the particle diameter regulating line as shown in FIG. 2 so that they could direct and receive laser beam to and from the liposome suspension flowing through the particle diameter regulating line.

(2) Correction of the Particle Diameter Monitoring System

The particle diameter regulating line was washed with about 5 liters of water. During this washing process, the light transmittance of laser was measured and the thus measured value was regarded as 100% for correction of the particle diameter monitoring system.

(3) Homogenizing Step

HSPC and cholesterol were weighed so that their molar ratio was 54:46, with the total amount of lipids being 82.5 mmol, 62.8 mmol, 41.2 mmol and 20.7 mmol. Absolute ethanol (about 50 mL) was added to the lipids, followed by heating for dissolution.

(4) Step of Preparing Crude Liposomes

A solution of ammonium sulfate (250 mM) was prepared. To the solution prepared in the homogenizing step was added the ammonium sulfate solution (heated to 65 to 75° C.) so that the resulting solution contained 10% ethanol.

(5) Step of Particle Diameter Regulation

The crude liposomes obtained in the step of preparing crude liposomes was incorporated into the particle diameter regulating line. In this step, polycarbonate filters, each having a pore diameter of 0.2 and 0.1 μm, were used in combination to regulate the particle diameter. Sampling (10 mL) was performed in each stage of particle diameter regulation. Incidentally, during the particle diameter regulating step, the sample solution was fed at a pressure of 10 MPa. The results are shown in FIG. 11.

(6) Step of Modification with a Hydrophilic Polymer

The previously prepared aqueous solution containing 7.69 g of $PEG_{5000}$-DSPE in 200 mL of RO water, which had been heated to 65° C., was added to the sample of liposomes obtained in the particle diameter regulating step. The resulting dispersion was heated at 60 to 70° C. so that $PEG_{5000}$-DSPE (0.75 mol %) was introduced into liposomes. After the heating was over, the liposome dispersion was cooled rapidly with ice.

Figure 11:
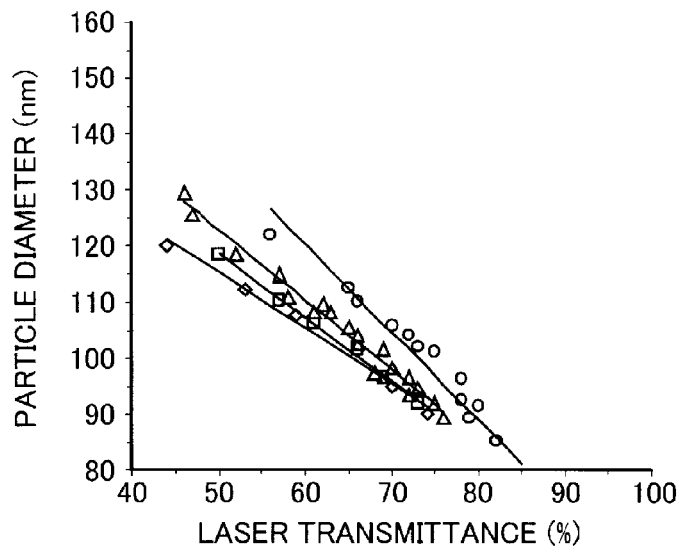
FIG. 11 is a graph showing the influence of lipid concentration on the relationship between the laser transmittance and the particle diameter of liposomes.

FIG. 11 is a graph showing the influence of lipid concentration on the relationship between the laser transmittance and the particle diameter of liposomes.

It is apparent from FIG. 11 that there is a high correlation, with the correlation coefficient being higher than 0.9, regardless of lipid concentrations even though the slope becomes slightly gentle as the lipid concentration increases.

Thus, the fact that there is a good linear relationship between the particle diameter and the laser transmittance regardless of lipid concentration suggests that it will be possible to predict the particle diameter from the laser transmittance.

Example 3

Accuracy of Prediction of Particle Diameter by the Particle Diameter Monitoring System Utilizing the Apparatus for Producing Liposomes According to the Present Invention (1) Mounting of Particle Diameter Monitoring System After the particle diameter regulating line for continuous operation was assembled as shown in FIG. 8, it was equipped with the particle diameter monitoring system as shown in FIG. 2, so as to construct the apparatus for producing liposomes. That is, the extruder was set in the filter holder (not shown), and the lasers were attached to the inlet and the outlet of the filter holder of the particle diameter regulating line as shown in FIG. 2 so that they could direct and receive laser beam to and from the liposome suspension flowing through the particle diameter regulating line.

(2) Correction of the Particle Diameter Monitoring System

The particle diameter regulating line was washed with about 5 liters of water. During this washing process, the light transmittance of laser was measured and the thus measured value was regarded as 100% for correction of the particle diameter monitoring system.

(3) Homogenizing Step

HSPC and cholesterol were weighed so that their molar ratio was 54:46, with the total amount of lipids being 82.5 mmol. Absolute ethanol was added to the lipids such that the ratio of the former to the latter is 1 mL to 1 g, approximately. The lipids were dissolved in ethanol by heating.

(4) Step of Preparing Crude Liposomes

A solution of ammonium sulfate (250 mM) was prepared. To the solution prepared in the homogenizing step was added the ammonium sulfate solution heated to 65 to 75° C. so that the resulting solution contained 10% ethanol.

(5) Step of Particle Diameter Regulation

Figure 12:
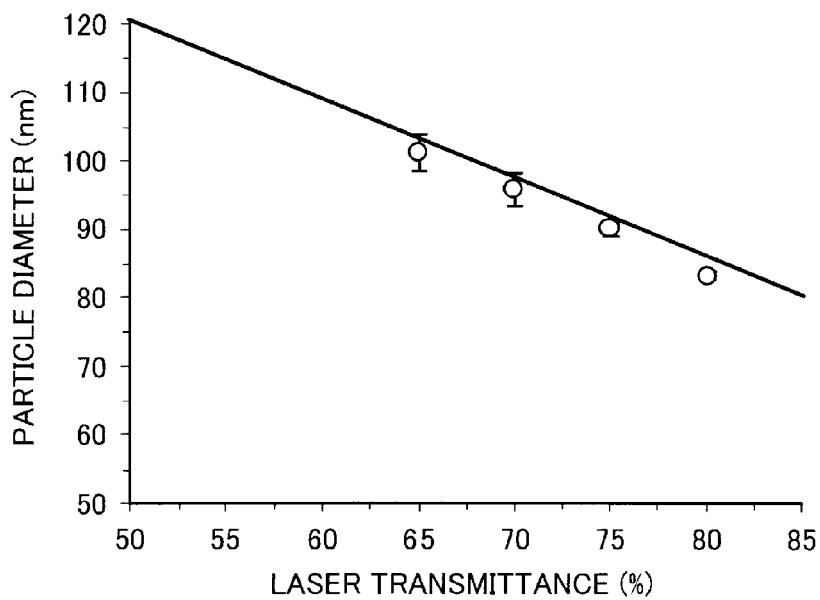
FIG. 12 is a graph showing the accuracy of the particle diameter monitoring system.

The particle diameter regulating line for continuous operation was assembled as shown in FIG. 8. The crude liposomes obtained in the step of preparing crude liposomes was incorporated into the particle diameter regulating line for continuous operation. In this step, polycarbonate filters, each having a pore diameter of 0.4, 0.2, and 0.1 μm, were used in combination to regulate the particle diameter. Sampling (10 mL) was performed when the laser transmittance reached 65, 70, 75, and 80%. Incidentally, during the particle diameter regulating step, the sample solution was fed at a pressure of 10 MPa. The results are shown in FIG. 12.

(6) Step of Modification with a Hydrophilic Polymer

The previously prepared aqueous solution containing 7.69 g of $PEG_{5000}$-H-DSPE in 200 mL of RO water, which had been heated to 65° C., was added to the sample of liposomes obtained in the particle diameter regulating step. The resulting dispersion was heated at 60 to 70° C. so that $PEG_{5000}$-DSPE was introduced into liposomes. (The amount introduced was 0.75 mol %.) After the heating was over, the liposome dispersion was cooled rapidly with ice.

This example was carried out under the same conditions as in Example 1 except that the particle diameter regulating line for batchwise operation was replaced by the one for continuous operation.

This example is intended to investigate how much the results deviate from the linear formula (shown in FIG. 10) if sampling is made when the transmittance is 65, 70, 75, or 80%. To achieve this object, Example 1 was carried out as a preliminary step, and this example was carried out as the main step in which the formula for prediction of particle diameter (which was obtained in FIG. 10 from the results of Example 1) is used as the index for correlation and the particle diameter monitoring system is installed in the apparatus for particle diameter regulation as shown in FIG. 2.

FIG. 12 is a graph showing the accuracy of the particle diameter monitoring system. In FIG. 12, the straight line is that obtained in FIG. 10, and the four plots represent the observations of particle diameter of samples taken when the transmittance reached 65, 70, 75 and 80%.

It is apparent from FIG. 12 that the observations are on the line of the formula for prediction of particle diameters at any value of laser transmittance.

This suggests that it is possible to accurately predict the particle diameter from the laser transmittance.

Example 4

Apparatus for Producing Liposomes According to the Present Invention (1) Mounting of Particle Diameter Monitoring System After the particle diameter regulating apparatus for continuous operation as shown in FIG. 1 was assembled, it was installed in the filter holder (not shown). It was equipped with the apparatuses for measuring light transmittance at the inlet and outlet of the filter holder of the particle diameter regulating line as shown in FIG. 1. In this way there was constructed the apparatus for producing liposomes according to the present invention.

(2) Correction of the Particle Diameter Monitoring System

The particle diameter regulating line was washed with about 5 liters of water. During this washing process, the light transmittance of laser was measured and the thus measured value was regarded as 100% for correction of the particle diameter monitoring system.

(3) Homogenizing Step

HSPC and cholesterol were weighed so that their molar ratio was 54:46, with the total amount of lipids being 82.5 mmol. Absolute ethanol was added to the lipids so that the ratio of the former to the latter was 1 mL to 1 g, approximately. The lipids were dissolved in ethanol by heating.

(4) Step of Preparing Crude Liposomes

A solution of ammonium sulfate (250 mM) was prepared. To the solution prepared in the homogenizing step was added the ammonium sulfate solution (heated to 65 to 75° C.) so that the resulting solution contained 10% ethanol.

(5) Step of Particle Diameter Regulation

Figure 13:
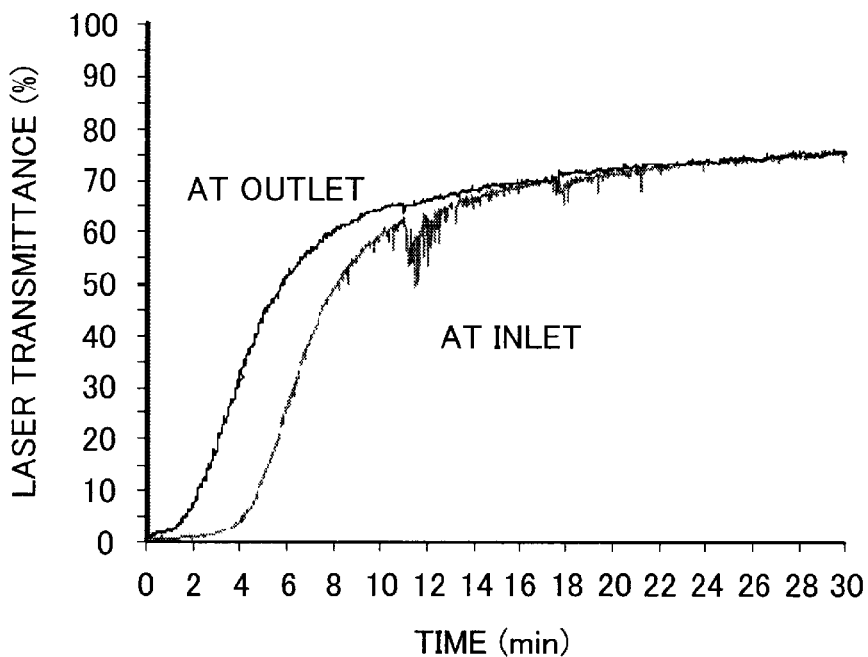
FIG. 13 is a graph showing the transition of the laser transmittance when setting the monitoring system of particle diameter illustrated in FIG. 1 and doing the particle diameter regulation of liposomes according to the continuously particle diameter regulation method which is the particle regulation of liposomes was continuously processed.
Figure 14:
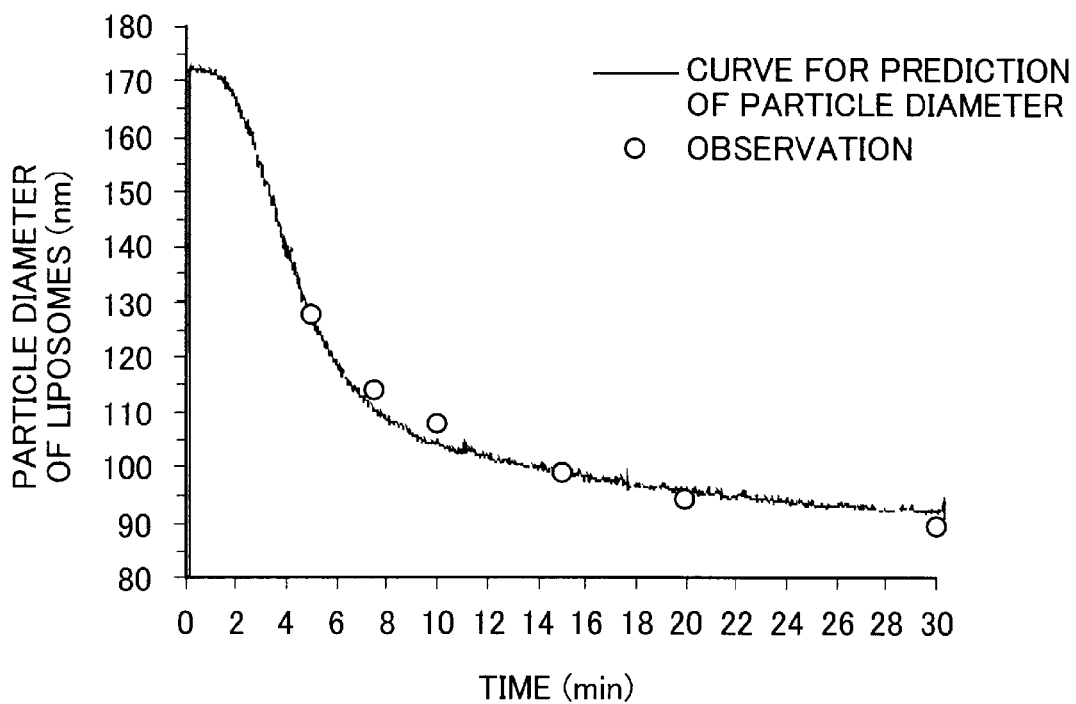
FIG. 14 is a graph showing the observation of particle diameter obtained and prediction curve of particle diameter according to the continuously particle regulation method, respectively.

The crude liposomes obtained in the step of preparing crude liposomes was incorporated into the apparatus for producing liposomes (or the particle diameter regulating line). In this step, polycarbonate filters, each having a pore diameter of 0.4, 0.2, and 0.1 μm, were used in combination to regulate the particle diameter. Incidentally, during the particle diameter regulating step, the sample solution was fed at a pressure of 10 MPa. After the start of particle diameter regulation, samples (10 mL) were taken at certain time intervals. The results are shown in FIGS. 13 and 14.

(6) Step of Modification with a Hydrophilic Polymer

The previously prepared aqueous solution containing 7.69 g of $PEG_{5000}$-DSPE in 200 mL of RO water, which had been heated to 65° C., was added to the sample of liposomes obtained in the particle diameter regulating step. The resulting dispersion was heated so that $PEG_{5000}$-DSPE was introduced into liposomes. (The amount introduced was 0.75 mol %.) After the heating was over, the liposome dispersion was cooled rapidly with ice.

This example demonstrated the liposome particle diameter control method by continuous operation that the liposomes was continuously processed to measure the transmittance of laser beam in the apparatus for the liposome production equipped with the particle diameter monitoring system shown in FIG. 1.

FIG. 13 graphically shows the change with time of the transmittance of laser beam measured at the outlet and inlet of the particle diameter regulating unit (extruder).

This example demonstrated the change with time of particle diameter by converting the transmittance of laser beam into the predicted particle diameter calculated from the formula shown in FIG. 10. This example also showed the result of an investigation on the accuracy of the predicted particle diameter relative to the observation of particle diameter of samples taken at certain time intervals. The result of this investigation is shown in FIG. 14, which is a graph showing the predicted particle diameter and the observations obtained by the continuous particle diameter regulating method.

It has not been elucidated how the formation of liposomes changes with time when the particle diameter regulation is accomplished continuously. In fact, particle diameter changes with time quite differently as shown in FIG. 9 even though continuous particle diameter regulation is accomplished under the same conditions. Therefore, it was very difficult to set up an adequate duration of the step of continuous particle diameter regulation in terms of time alone.

However, according to the method of the present invention, the state of the sample being processed is shown in terms of the transmittance of laser beam, and the change with time of the transmittance can be monitored in a non-contact manner.

The particle diameter monitoring systems installed at the inlet and the outlet observe how liposomes differ in laser transmittance before and after they pass through the particle diameter regulating unit (that part shown as the extruder in this example).

Further, the laser transmittance is a parameter that can be converted into the particle diameter by using the formula for prediction of particle diameter; consequently, the difference in particle diameter before and after particle diameter regulation may be judged in the course of production. In other words, the difference in particle diameter can be adopted as a converging point in the particle diameter regulation step, and can be utilized for setting of and as an end point in the particle diameter regulation step.

FIG. 14 is a graph showing the relationship between the reduction curve for the predicted particles in the continuous particle diameter regulating step (the curve being obtained from the laser transmittance according to the formula for prediction obtained in FIG. 10) and the particle diameter of liposomes at 5, 7.5, 10, 15, 20, and 30 minutes. This result indicates that the actually measured particle diameter nearly coincides with the predicted one and hence the particle diameter monitoring system achieves very good prediction.

Example 5

Influence on Predictability of the Flow Velocity in Particle Diameter Regulating Step in the Apparatus for Producing Liposomes According to the Present Invention (1) Mounting of Particle Diameter Monitoring System After the particle diameter regulating line was assembled as shown in FIG. 1, and the particle diameter regulating apparatus was installed in the filter holder (not shown). The light transmittance measuring apparatuses were attached to the inlet and the outlet of the filter holder of the particle diameter regulating line as shown in FIG. 1. In this way the apparatus for producing liposomes according to the present invention was constructed.

(2) Correction of the Particle Diameter Monitoring System

The particle diameter regulating line was washed with about 5 liters of water. During this washing process, the light transmittance of laser was measured and the thus measured value was regarded as 100% for correction of the particle diameter monitoring system.

(3) Homogenizing Step

HSPC and cholesterol were weighed so that their molar ratio was 54:46, with the total amount of lipids being 41.2 mmol. Absolute ethanol (about 50 mL) was added to the lipids, followed by heating for dissolution.

(4) Step of Preparing Crude Liposomes

A solution of ammonium sulfate (250 mM) was prepared. To the solution prepared in the homogenizing step was added the ammonium sulfate solution (heated to 65° C. or higher) so that the resulting solution contained 10% ethanol.

(5) Step of Particle Diameter Regulation

Figure 15:
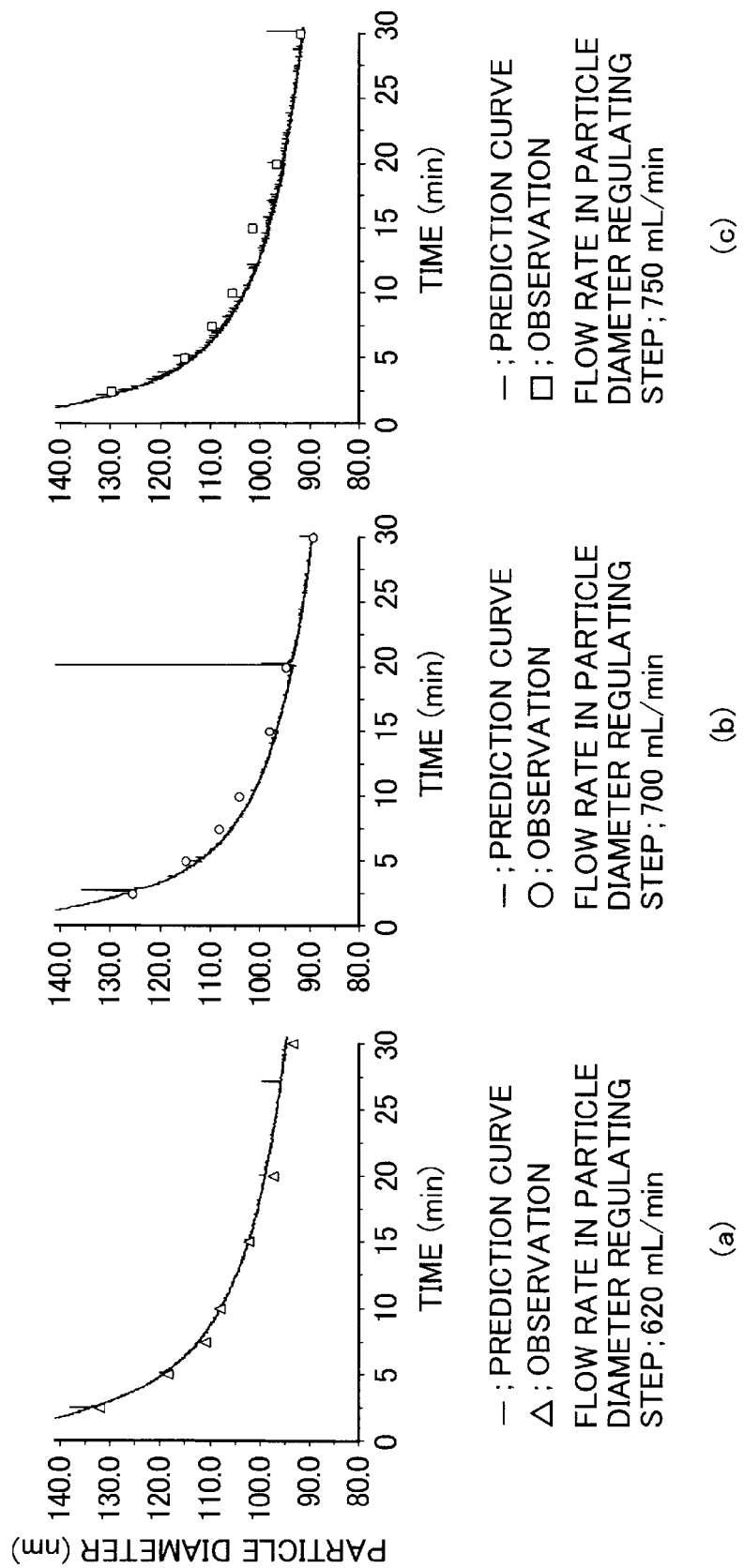
FIG. 15 is graphs each showing the observation of particle diameter obtained and prediction curve of particle diameter (solid line) according to the continuously particle regulation method, respectively.

The continuous particle diameter regulating apparatus was assembled as shown in FIG. 1. The crude liposomes obtained in the step of preparing crude liposomes was incorporated into the particle diameter regulating line. In this step, polycarbonate filters, each having a pore diameter of 0.4, 0.2, and 0.1 µm, were used in combination to regulate the particle diameter. The flow rate of water was adjusted to 620, 700, and 750 mL/min. Sampling (10 mL) was performed at certain time intervals after the start of particle diameter regulation. The results are shown in FIG. 15.

(6) Step of Modification with a Hydrophilic Polymer

The previously prepared aqueous solution containing 7.69 g of $PEG_{5000}$-DSPE in 200 mL of RO water, which had been heated to 65° C., was added to the sample of liposomes obtained in the particle diameter regulating step. The resulting dispersion was heated so that $PEG_{5000}$-DSPE was introduced into liposomes. (The amount introduced was 0.75 mol %.) After the heating was over, the liposome dispersion was cooled rapidly with ice.

The actual rate of particle diameter regulation varies depending on the formulation of liposomes and how liposomes are produced in the step of forming crude liposomes even though it is possible to keep constant the conditions in the particle diameter regulation step. In this example, FIG. 15 showed the differences of the observation of particle diameter from the prediction curve, which converted from the transmittance of laser pertaining to the present invention to show the change in particle diameter when particle diameter regulation step was conducted at different rate. FIG. 15 is a graph showing the observation of particle diameter and the prediction curve of particle diameter (solid line) according to the continuous particle regulation method.

In this example, sampling was performed at a timing of 5, 7.5, 10, 15, 20, and 30 minutes after the start of continuous particle diameter regulation under all the conditions. The thus obtained samples were examined for the particle diameter (observation) of liposomes. There was no noticeable difference between the observation and the predicted value at any timing. It has been mentioned above that, according to the present invention, there exists a high correlation between the laser transmittance and the particle diameter of liposomes. The result of this example clearly indicates that this predictability is not affected by the flow rate in the apparatus (FIG. 15).

It was shown that the present invention makes it possible to measure the particle diameter not only during particle diameter regulation in batchwise operation but also during particle diameter regulation in continuous operation. It was also shown that the particle diameter monitoring system according to the present invention makes it possible to produce liposomes with any particle diameter desired and under any conditions.

Example 6

Prediction of Particle Diameter and Application Thereof by Means of the Apparatus for Producing Liposomes According to the Present Invention According to the present invention, the light transmittance measuring apparatuses are arranged in front and behind the extruder, as shown in FIG. 1. This arrangement makes it possible to monitor the behavior of the particle diameter of liposomes in front and behind the extruder as shown in FIG. 13. This example is intended to verify whether it is possible to predict the particle size distribution of liposomes from the change in particle diameter that is observed in front and behind the extruder.

Example 6 demonstrates experiments carried out in the same way as in Example 4. The results are shown in FIGS. 16 and 17.

Figure 16:
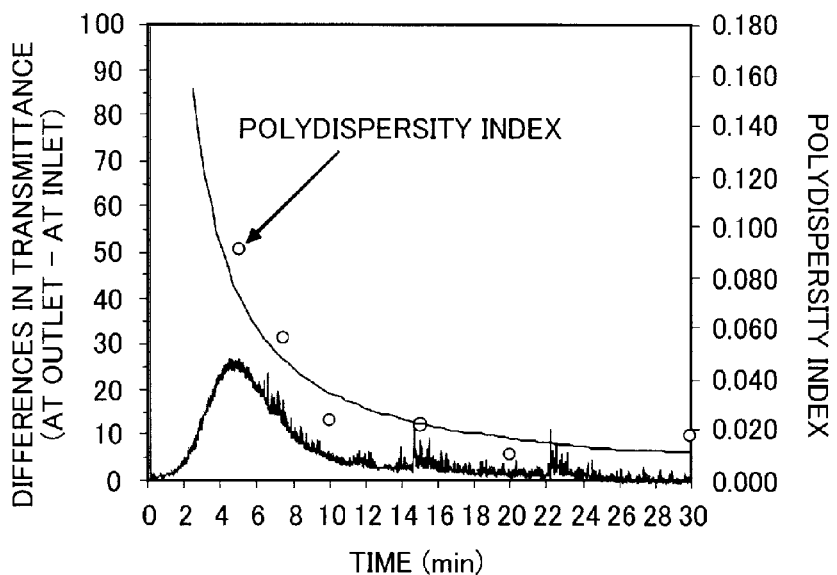
FIG. 16 is a graph showing the relationship between the laser transmittance and the particle size distribution of liposomes (measured by dynamic light scattering).
Figure 17:
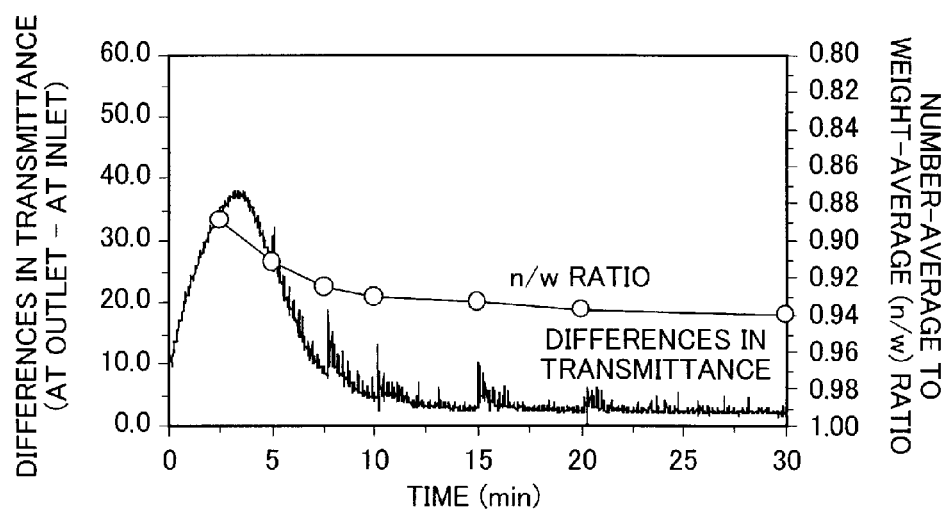
FIG. 17 is a graph showing the relationship between the laser transmittance and the particle size distribution of liposomes (measured by FFF-MALS).

FIGS. 16 and 17 are graphs showing the relationship between the differences in laser transmittance measured at the inlet and outlet of the particle diameter regulating apparatus and the particle size distribution of liposomes. According to the present invention, the particle size distribution is expressed in terms of polydispersity index (FIG. 16) measured by dynamic light scattering or in terms of n/w ratio (FIG. 17) obtained from FFF-MALS. Incidentally, the particle size distribution becomes narrower as the polydispersity index decreases or the n/w ratio comes closer to 1.

As shown in FIGS. 16 and 17, it was clarified that the differences in transmittance increase just after particle diameter regulation and it reaches a maximum, gradually decreases, and finally approaches zero according as particle diameter regulation proceeds. It was found that this trend relates with the index of particle size distribution. In other words, it is apparent that there is a correlation between the differences in transmittance and the index of particle size distribution and that the particle size distribution of liposomes decreases with a decrease in the differences in transmittance.

As mentioned above, the control of particle diameter of liposomes is an important step in the production process of liposomes. The particle diameter of liposomes is a factor that affects the behavior of liposomes in blood and the accumulation of liposomes in lesions. Although liposome particles are usually denoted in terms of average particle diameter, the pharmaceutical preparations of liposomes are expected to vary in characteristic properties depending on the particle size distribution even though they are the same in average particle diameter. Therefore, the particle size distribution is an important parameter that determines the quality of pharmaceutical preparations of liposomes. Accordingly, it is necessary to consider the particle size distribution to ensure uniform quality for pharmaceutical preparations of liposomes. There is no useful method for evaluating the particle size distribution during the particle diameter regulation step. One reason for this is that it is impossible to determine the particle diameter in real time during the particle diameter regulation step. However, the present invention makes it possible to determine in real time in a simple manner the particle diameter before and after the sample solution passes through the extruder. Moreover, it makes it possible to evaluate the state of particles in a simple manner from the particle diameter measured in front and behind the extruder. Although it is very difficult to predict the particle size distribution, not to mention the particle diameter, in the continuous particle diameter regulating step, it was found that the method of the present invention makes it possible to predict not only the particle diameter but also the particle size distribution.

Controlling the particle diameter of liposomes by batchwise operation has been a common commercial practice. The apparatus for particle diameter regulation according to the present invention makes it possible to produce liposomes having a uniform particle diameter in the production of pharmaceutical preparations of liposomes which involves difficulties in taking validation in controlling the particle diameter due to the fact that there is no correlation between the duration of work for particle diameter regulation and the resulting particle diameter. Moreover, the method of the present invention obviates the necessity of taking samples in real time from the tank or the like and permits the measurement of particle diameter in a non-contact manner. This will facilitate the detection of poor quality and anomalous step in the course of manufacturing process, and it will also minimize the germ-related risk.

Example 7

Production of Liposomes to Support Drugs

Listed below are the abbreviation and molecular weight of each component used in the examples.
Hydrogenated soybean lecithin (HSPC, M.W. 790)
Cholesterol (M.W. 386.66)
Polyethylene glycol$_{5000}$-distearoylphosphatidyldiethanolamine (PEG$_{5000}$-DEPE, M.W. 6031)
3,5-dipentadecyloxybenzamidine hydrochloride (TRX-20, M.W. 609.41)
Drug: prednisolone phosphate (M.W. 440)
This example was carried out with the following apparatuses.
Apparatus for measurement of light transmittance: Model LX2-V10, for laser, made by Keyence Corp.

Data collection device: Model NR-HA08, NR-500 made by Keyence Corp.
Wavelength of laser used in this example: 670 nm (1) Mounting of Particle Diameter Monitoring System After the continuous particle diameter regulating line was assembled as shown in FIG. 8, it was equipped with the particle diameter monitoring system as shown in FIG. 2. That is, the extruder was mounted in the filter holder (not shown), and the apparatuses for measuring light transmittance were attached to the inlet and outlet of the filter holder of the particle diameter regulating line as shown in FIG. 2 so that they could direct and receive laser beam to and from the suspension of liposomes flowing through the particle diameter regulating line.

(2) Correction of the Particle Diameter Monitoring System

The particle diameter regulating line was washed with about 5 liters of water. During this washing process, the light transmittance of laser was measured and the thus measured value was regarded as 100% for correction of the particle diameter monitoring system.

(3) Homogenizing Step

HSPC, cholesterol, and TRX-20 were weighed so that their molar ratio was 50:42:8, with the total amount of lipids being 84.8 mmol. Absolute ethanol (about 50 mL) was added to the lipids, followed by heating for dissolution.

(4) Step of Preparing Crude Liposomes

An aqueous solution of prednisolone phosphate (68.0 mg/mL) was prepared. To the solution prepared in the homogenizing step was added the aqueous solution heated at 65 to 70° C. so that the resulting solution contained 10% ethanol.

(5) Step of Particle Diameter Regulation

The crude liposomes obtained in the step of preparing crude liposomes was incorporated into the particle diameter regulating line. In this step, polycarbonate filters, each having a pore diameter of 0.4, 0.2, and 0.1 μm, were used in combination to regulate the particle diameter. The light transmittance was measured from time to time by using the apparatus for measuring light transmittance. The data collecting device displayed the particle diameter of liposomes which it had calculated by using the above-mentioned correlation.

Samples (10 mL each) were taken from the liposome-containing solution under processing at time intervals of 2.5, 5, 7.5, 10, 15, and 30 minutes after the start of the particle diameter regulating step. The samples were examined for the particle diameter of liposomes in the liposome-containing solution under processing. Thus there were obtained observations of liposome particle diameter.

Figure 19:
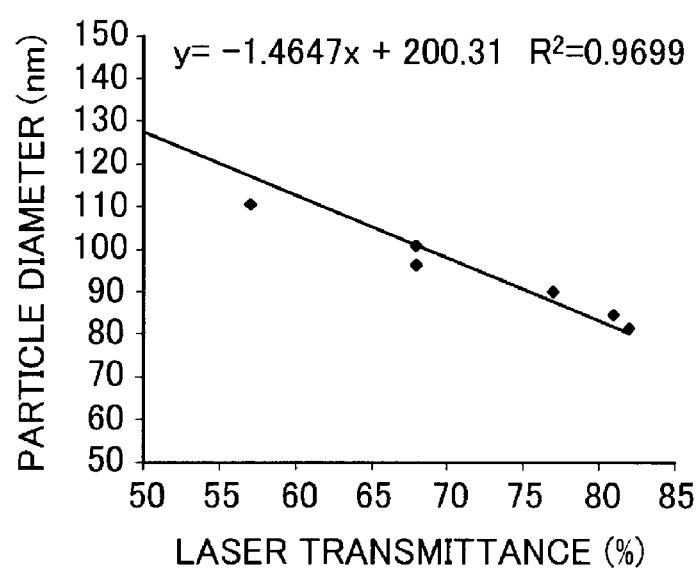
FIG. 19 is a graph showing the relationship between the particle diameter and the laser transmittance.

Incidentally, during the particle diameter regulating step, the sample solution was fed at a pressure of 10 MPa. The results are shown in FIG. 19.

(6) Step of Modification with a Hydrophilic Polymer

The previously prepared aqueous solution containing 3.85 g of PEG$_{5000}$-DSPE in 100 mL of RO water, which had been heated to 65° C., was added to the sample of liposomes obtained in the particle diameter regulating step. The resulting dispersion was heated at 60 to 70° C. so that PEG$_{5000}$-DSPE was introduced into liposomes. (The amount introduced was 0.75 mol %.) After the heating was over, the liposome dispersion was cooled rapidly with ice.

Figure 18:
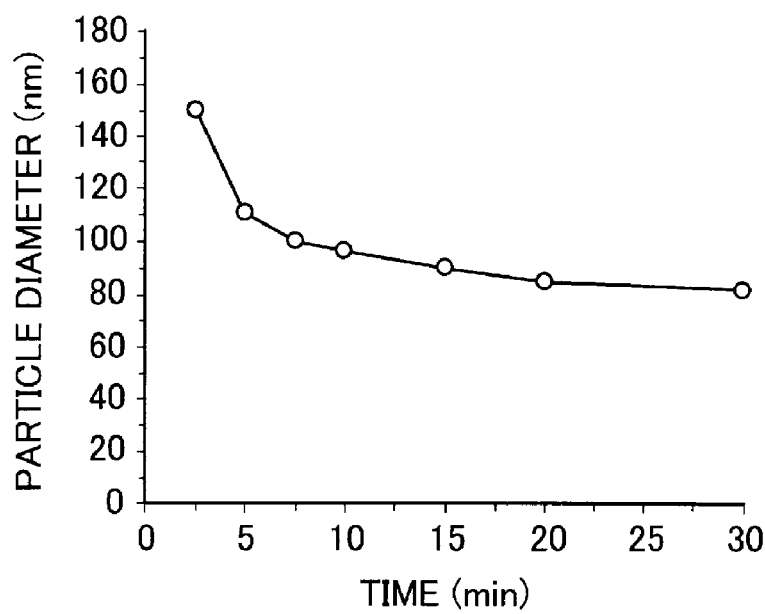
FIG. 18 is a graph showing the relationship between the duration in particle diameter regulation step and the particle diameter of the drug-containing liposomes which have undergone particle diameter regulation according to continuously particle diameter regulation method.

FIG. 18 is a graph showing the relationship between the duration in particle diameter regulation step and the particle diameter of liposomes which have undergone continuous particle diameter regulation according to the formulation mentioned above.

It is apparent from FIG. 18 that in the production of drug-carrying liposomes, the particle diameter of liposomes decreases with the duration of particle diameter regulation in the same way as in the production of drug-free liposomes.

In the case where the concentration of liposome-forming lipids contained in the solution under processing which contains liposome-forming lipids is 171.6 mmol/L and the concentration of drugs contained in the solution under processing which contains liposome-forming lipids is 15.5 mmol/L, the correlation between the light transmittance of the liposome-containing solution and the particle diameter of liposomes contained in the liposome-containing solution is expressed by the formula below:

Particle diameter=−1.4647×laser transmittance+ 200.31;Correlation($r^2$)=0.9699(See FIG. 19).

Figure 20:
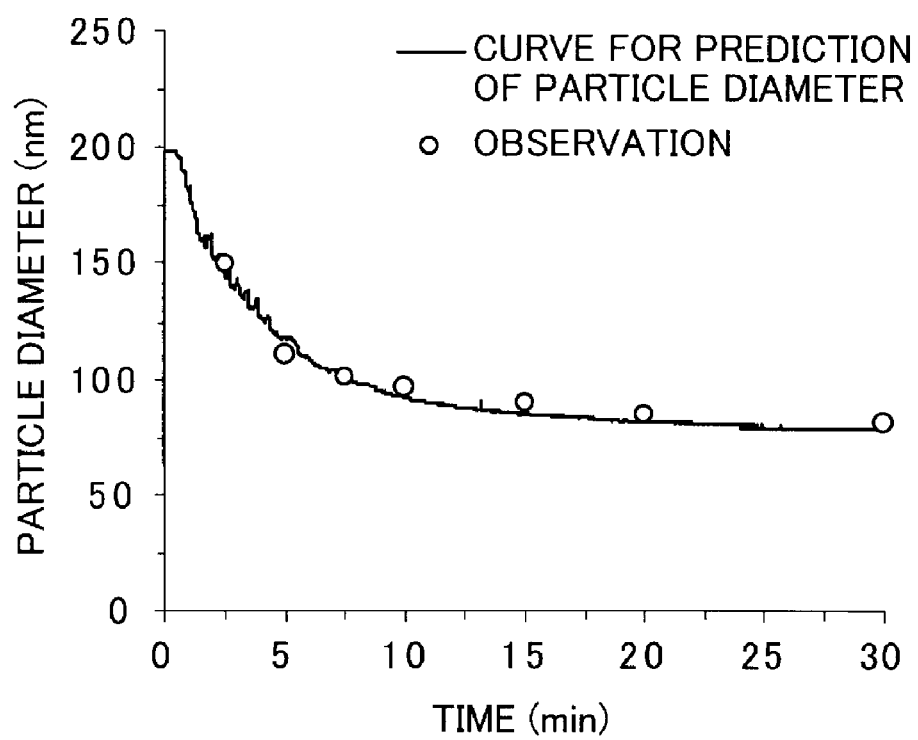
FIG. 20 is a graph showing the observation of particle diameter obtained and prediction curve of particle diameter (solid line) according to the continuously particle regulation method, respectively.

FIG. 20 is a graph showing time variations of the observation of particle diameter of liposomes (contained in the liposome-containing solution under processing) and prediction curve particle diameter of liposomes (contained in the liposome-containing solution under processing), measured in the production of drug-carrying liposomes by the apparatus for producing liposomes according to the present invention. Incidentally, in this example, the particle diameter was predicted from the formula below:

Particle diameter=−1.4647×laser transmittance+ 200.31.

It is apparent from FIG. 20 that in the case where drug-enclosed liposomes are produced by using the apparatus for producing liposomes according to the present invention, the observation of particle diameter of liposomes in the liposome-containing solution under processing nearly coincides with the prediction curve.

Therefore, the apparatus for producing liposomes according to the present invention, which is so designed as to monitor the light transmittance of the solution under processing which contains drug-enclosed liposomes, is capable of producing drug-enclosed liposomes in line under sterile conditions.

DESCRIPTION OF REFERENCE NUMERALS 100, 200, 701, 801: Apparatus for producing liposomes
110, 220, 720, 820: Unit for particle diameter regulation
168, 164, 883, 887: Terminal end
162, 166, 885, 881: Base end
112, 221, 711, 713, 811: Inlet
114, 223, 715, 717, 813: Outlet
122, 201, 731, 751, 831: Supply flow channel
124, 202, 733, 753, 833: Discharge flow channel
127, 205, 739, 841: Input port
128, 204, 741, 851: First light transmitting part
126, 203, 853: Second light transmitting part
761, 763, 765: Second to fourth light transmitting part
129, 157, 206, 740, 746, 843: Valve
152, 743, 755, 861: Tank
154, 735, 871: Pump
156, 745: Discharge port
132, 213: First unit for measuring light transmittance
134, 211: Second unit for measuring light transmittance
140, 230: Apparatus for measuring particle diameter of liposomes
889: Fluid recycling circuit
142, 215: Control unit
144, 217: Data storage device
146, 219: Data collecting device
147, 148, 231, 233: Cord
301, 401, 501: Flow channel
303, 503: Inside
307, 509, 737, 873: Arrow
305, 505: Light transmitting part
321, 521, 523: Light
325: Part irradiated with light 321
310: Unit for measurement of light transmittance
311, 411: Light irradiating part
313, 413: Light receiving part
323: Light which has passed through the light transmitting part 305
330, 530: Liposome-containing solution under processing
315, 317, 415, 417, 515, 517: Cord
L3: Outside diameter of flow channel 401
L1: Space between light irradiating part 411 and flow channel 401
L2: Space between light receiving part 413 and flow channel 401
506: Light irradiating part
507: Light passing part
511: Light irradiating part that emits light 521
513: Light receiving part that receives light 523
601, 602: Liposome production line

The invention claimed is:

1. An apparatus for producing liposomes, comprising:
a particle diameter regulating unit for regulating the particle diameter of liposomes by membrane emulsification or shear force emulsification, the particle diameter regulating unit having an inlet and an outlet;
a supply flow channel to supply the particle diameter regulating unit with a solution under processing containing a liposome-forming lipid, the supply flow channel being formed integrally with the particle diameter regulating unit through the inlet;
a discharge flow channel to discharge from the particle diameter regulating unit a liposome-containing solution under processing containing the liposomes, the discharge flow channel being formed integrally with the particle diameter regulating unit through the outlet;
the supply flow channel having an input port through which the solution under processing containing the liposome-forming lipid is put into the supply flow channel;
wherein the discharge flow channel has a first light-transmitting part at least a portion of which is made of material transparent to light, and
also has at least a first light transmittance measuring unit which measures the light transmittance of the liposome-containing solution under processing by directing light to the first light-transmitting part from the outside of the first light-transmitting part; and
the first light-transmitting part and the first light transmittance measuring unit obtaining the particle diameter of liposomes contained in the liposome-containing solution under processing by utilizing a preliminarily acquired correlation between the light transmittance and the particle diameter of liposomes which is applied to the measured light transmittance of the liposome-containing solution.

2. The apparatus for producing liposomes as defined in claim 1, wherein a base end of the supply flow channel and a terminal end of the discharge flow channel are joined together so as to complete a circulating circuit for fluid.

3. The apparatus for producing liposomes as defined in claim 1, wherein the supply flow channel has a second light-transmitting part at least a portion of which is made of material transparent to light, and
also has a second light transmittance measuring unit which measures the light transmittance of the solution under processing containing the liposome-forming lipid by directing light to the second light-transmitting part from the outside of the second light-transmitting part.

4. The apparatus for producing liposomes as defined in claim 3, wherein the first light transmittance measuring unit has a first laser irradiating part, a first laser receiving part, and a first light transmittance calculating part connected to them, and the second light transmittance measuring unit has a second laser irradiating part, a second laser receiving part, and a second light transmittance calculating part connected to them.

5. The apparatus for producing liposomes as defined in claim 1, which further comprises a unit for calculating the particle diameter of liposomes from the light transmittance.

6. The apparatus for producing liposomes as defined in claim 3, wherein the first light transmittance measuring unit displays the light transmittance of the liposome-containing solution under processing and the second light transmittance measuring unit displays the light transmittance of the solution under processing containing said liposome-forming lipid.

7. A method of producing liposomes comprising:
a preliminary step including passing a solution containing a liposome-forming lipid several times through a particle diameter regulating unit, thereby giving a liposome-containing solution, examining each liposome-containing solution, which has passed through the particle diameter regulating unit, for the light transmittance at a prescribed wavelength, examining with a granulometer each liposome-containing solution, which has passed through the particle diameter regulating unit, for the particle diameter of liposomes in the liposome-containing solution, and acquiring preliminarily the correlation between the light transmittance and the particle diameter; and a main step including causing the solution under processing containing a liposome-forming lipid to undergo particle diameter regulation by the apparatus for producing liposomes as defined in claim 1, thereby giving the liposome-containing solution under processing, and producing liposomes while measuring the light transmittance of the liposome-containing solution under processing at the prescribed wavelength.

* * * * *